US010456557B2

(12) United States Patent
Guala et al.

(10) Patent No.: US 10,456,557 B2
(45) Date of Patent: Oct. 29, 2019

(54) OCCLUSION BYPASSING APPARATUS WITH VARYING FLEXIBILITY AND METHODS FOR BYPASSING AN OCCLUSION IN A BLOOD VESSEL

(71) Applicant: Invatec S.p.A., Roncadelle (IT)

(72) Inventors: Carlo Guala, Roncadelle (IT); Claudio Silvestro, Roncadelle (IT); Massimo Morero, Roncadelle (IT); Giovanni Scalvini, Roncadelle (IT)

(73) Assignee: Invatec S.p.A., Roncadelle (IT)

( * ) Notice: Subject to any disclaimer, the term of this patent is extended or adjusted under 35 U.S.C. 154(b) by 16 days.

(21) Appl. No.: 14/460,048

(22) Filed: Aug. 14, 2014

(65) Prior Publication Data
US 2016/0045219 A1 Feb. 18, 2016

(51) Int. Cl.
A61M 25/01 (2006.01)
A61B 17/22 (2006.01)
(Continued)

(52) U.S. Cl.
CPC ......... *A61M 25/0194* (2013.01); *A61B 17/22* (2013.01); *A61B 17/3478* (2013.01);
(Continued)

(58) Field of Classification Search
CPC ...... A61M 25/0194; A61M 2025/0197; A61B 17/3478; A61B 2017/00309;
(Continued)

(56) References Cited

U.S. PATENT DOCUMENTS 4,552,554 A 11/1985 Gould et al.
4,774,949 A 10/1988 Fogarty
(Continued)

FOREIGN PATENT DOCUMENTS

EP 1765193 10/2012
JP 2002525163 8/2002
(Continued)

OTHER PUBLICATIONS

PCT/US2015/044239, The International Search Report and the Written Opinion of the International Searching Authority, dated Sep. 25, 2015.
U.S. Appl. No. 13/952,973, filed Jul. 29, 2013, Silvestro.
U.S. Appl. No. 13/952,981, filed Jul. 29, 2013, Silvestro.
U.S. Appl. No. 14/197,803, filed Mar. 5, 2014, Silvestro.
(Continued)

*Primary Examiner* — Ryan J. Severson
*Assistant Examiner* — Christian D Knauss
(74) *Attorney, Agent, or Firm* — Medler Ferro Woodhouse & Mills PLLC

(57) ABSTRACT

An occlusion bypassing apparatus is disclosed for re-entering the true lumen of a vessel after subintimally bypassing an occlusion in a vessel. The apparatus includes an outer shaft component, an inner shaft component disposed within the outer shaft component, and a needle component slidably disposed within the inner shaft component. The inner shaft component includes a body portion and a needle housing, which is distal to the body portion. The needle housing is less flexible than the body portion. In order to smooth the transition between the body portion and the needle housing, the needle housing includes a transition portion that has a variable flexibility along its length that decreases in a distal direction. A curved distal end of the needle component is distally advanced relative to the inner shaft component to pierce through the intima of the vessel and thereafter enter the true lumen.

17 Claims, 26 Drawing Sheets

(51) Int. Cl.
*A61B 17/34* (2006.01)
*A61M 25/10* (2013.01)
*A61B 17/00* (2006.01)
*A61B 90/00* (2016.01)
*A61M 25/00* (2006.01)

(52) U.S. Cl.
CPC .............. *A61M 25/1011* (2013.01); *A61B 2017/00309* (2013.01); *A61B 2017/22054* (2013.01); *A61B 2017/22069* (2013.01); *A61B 2017/22095* (2013.01); *A61B 2090/3966* (2016.02); *A61M 2025/0095* (2013.01); *A61M 2025/0197* (2013.01); *A61M 2025/1047* (2013.01); *A61M 2210/12* (2013.01)

(58) Field of Classification Search
CPC ........... A61B 2017/22054; A61B 2017/22069; A61B 2017/22094; A61B 2017/22095; A61B 17/3205
See application file for complete search history.

(56) References Cited

U.S. PATENT DOCUMENTS

| | | | |
|---|---|---|---|
| 5,002,532 | A | 3/1991 | Gaiser et al. |
| 5,047,045 | A | 9/1991 | Arney et al. |
| 5,217,434 | A | 6/1993 | Arney |
| 5,250,069 | A | 10/1993 | Nobuyoshi et al. |
| 5,304,134 | A | 4/1994 | Kraus et al. |
| 5,460,608 | A | 10/1995 | Lodin et al. |
| 5,501,667 | A | 3/1996 | Verduin, Jr. |
| 5,569,184 | A | 10/1996 | Crocker et al. |
| 5,599,324 | A | 2/1997 | McAlister et al. |
| 5,667,493 | A | 9/1997 | Janacek |
| 5,707,389 | A | 1/1998 | Louw et al. |
| 5,830,222 | A | 11/1998 | Makower |
| 5,916,194 | A | 6/1999 | Jacobsen et al. |
| 5,947,994 | A | 9/1999 | Louw et al. |
| 6,068,638 | A | 5/2000 | Makower |
| 6,071,292 | A | 6/2000 | Makower et al. |
| 6,081,738 | A | 6/2000 | Hinohara et al. |
| 6,159,225 | A | 12/2000 | Makower |
| 6,178,968 | B1 | 1/2001 | Louw et al. |
| 6,190,353 | B1 | 2/2001 | Makower et al. |
| 6,196,230 | B1 | 3/2001 | Hall et al. |
| 6,203,524 | B1 | 3/2001 | Burney et al. |
| 6,217,527 | B1 | 4/2001 | Selmon et al. |
| 6,221,049 | B1 | 4/2001 | Selmon et al. |
| 6,231,546 | B1 | 5/2001 | Milo et al. |
| 6,231,563 | B1 | 5/2001 | White et al. |
| 6,231,587 | B1 | 5/2001 | Makower et al. |
| 6,235,000 | B1 | 5/2001 | Milo et al. |
| 6,261,260 | B1 | 7/2001 | Maki et al. |
| 6,283,983 | B1 | 9/2001 | Makower et al. |
| 6,287,317 | B1 | 9/2001 | Makower et al. |
| 6,302,875 | B1 | 10/2001 | Makower et al. |
| 6,355,027 | B1 | 3/2002 | Le et al. |
| 6,375,615 | B1 | 4/2002 | Makower et al. |
| 6,379,319 | B1 | 4/2002 | Garibotto et al. |
| 6,432,127 | B1 | 8/2002 | Kim et al. |
| 6,447,477 | B2 | 9/2002 | Burney et al. |
| 6,458,098 | B1 | 10/2002 | Kanesaka |
| 6,508,824 | B1 | 1/2003 | Flaherty et al. |
| 6,511,458 | B2 | 1/2003 | Milo et al. |
| 6,514,217 | B1 | 2/2003 | Selmon et al. |
| 6,514,228 | B1 | 2/2003 | Hamilton et al. |
| 6,544,230 | B1 | 4/2003 | Flaherty et al. |
| 6,579,311 | B1 | 6/2003 | Makower |
| 6,602,241 | B2 | 8/2003 | Makower et al. |
| 6,655,386 | B1 | 12/2003 | Makower et al. |
| 6,669,709 | B1 | 12/2003 | Cohn et al. |
| 6,709,444 | B1 | 3/2004 | Makower |
| 6,719,725 | B2 | 4/2004 | Milo et al. |
| 6,726,677 | B1* | 4/2004 | Flaherty ............... A61B 1/3137 600/439 |
| 6,746,464 | B1 | 6/2004 | Makower et al. |
| 7,004,173 | B2 | 2/2006 | Sparks et al. |
| 7,059,330 | B1 | 6/2006 | Makower et al. |
| 7,066,914 | B2 | 6/2006 | Andersen |
| 7,141,041 | B2 | 11/2006 | Seward |
| 7,179,270 | B2 | 2/2007 | Makower et al. |
| 7,316,655 | B2 | 1/2008 | Garibotto et al. |
| 7,357,794 | B2 | 4/2008 | Makower et al. |
| 7,534,223 | B2 | 5/2009 | Boutilette et al. |
| 7,606,615 | B2 | 10/2009 | Makower et al. |
| 7,637,870 | B2 | 12/2009 | Flaherty et al. |
| 7,729,738 | B2 | 6/2010 | Flaherty et al. |
| 7,762,985 | B2 | 7/2010 | Kabrick et al. |
| 7,833,197 | B2 | 11/2010 | Boutilette et al. |
| 7,854,727 | B2 | 12/2010 | Belsley |
| RE42,049 | E | 1/2011 | Schroeder et al. |
| 7,878,986 | B2 | 2/2011 | Jen et al. |
| 7,879,004 | B2 | 2/2011 | Seibel et al. |
| 7,896,840 | B2 | 3/2011 | Spencer et al. |
| 7,938,819 | B2 | 5/2011 | Kugler et al. |
| 8,083,727 | B2 | 12/2011 | Kugler et al. |
| 8,147,507 | B2 | 4/2012 | Shturman |
| 8,172,863 | B2 | 5/2012 | Robinson et al. |
| 8,202,246 | B2 | 6/2012 | Kugler et al. |
| 8,221,357 | B2 | 7/2012 | Boutillette |
| 8,226,566 | B2 | 7/2012 | Nita |
| 8,241,311 | B2 | 8/2012 | Ward et al. |
| 8,257,382 | B2 | 9/2012 | Rottenberg et al. |
| 8,323,261 | B2 | 12/2012 | Kugler et al. |
| 8,337,425 | B2 | 12/2012 | Olson et al. |
| 8,388,876 | B2 | 3/2013 | Boutilette et al. |
| 8,460,254 | B2 | 6/2013 | Belsley |
| 8,460,316 | B2 | 6/2013 | Wilson et al. |
| 8,486,022 | B2 | 7/2013 | Ludwig et al. |
| 8,496,679 | B2 | 7/2013 | Robinson et al. |
| 8,512,310 | B2 | 8/2013 | Kugler et al. |
| 8,535,245 | B2 | 9/2013 | Jen et al. |
| 8,556,857 | B2 | 10/2013 | Boutillette |
| 9,095,374 | B2 | 8/2015 | Piccagli |
| 2001/0000041 | A1* | 3/2001 | Selmon ............... A61B 17/3207 600/585 |
| 2002/0072706 | A1 | 6/2002 | Hiblar et al. |
| 2004/0073165 | A1 | 4/2004 | Musbach et al. |
| 2004/0167554 | A1 | 8/2004 | Simpson et al. |
| 2004/0186506 | A1 | 9/2004 | Simpson et al. |
| 2005/0021003 | A1 | 1/2005 | Caso et al. |
| 2005/0149062 | A1* | 7/2005 | Carroll ............... A61B 17/3478 606/129 |
| 2005/0171478 | A1 | 8/2005 | Selmon et al. |
| 2005/0267459 | A1* | 12/2005 | Belhe ................. A61B 18/1492 606/41 |
| 2006/0074442 | A1 | 4/2006 | Noriega et al. |
| 2006/0094930 | A1 | 5/2006 | Sparks et al. |
| 2006/0241342 | A1 | 10/2006 | Macaulay et al. |
| 2006/0276749 | A1 | 12/2006 | Selmon et al. |
| 2008/0125748 | A1 | 5/2008 | Patel |
| 2008/0228171 | A1 | 9/2008 | Kugler et al. |
| 2009/0088685 | A1* | 4/2009 | Kugler ................. A61B 17/221 604/101.01 |
| 2009/0124899 | A1 | 5/2009 | Jacobs et al. |
| 2009/0156998 | A1 | 6/2009 | Arana et al. |
| 2009/0192584 | A1* | 7/2009 | Gerdts ...................... A61F 2/95 623/1.11 |
| 2010/0010522 | A1 | 1/2010 | Shturman |
| 2010/0063534 | A1 | 3/2010 | Kugler et al. |
| 2011/0144677 | A1 | 6/2011 | Ward et al. |
| 2011/0276079 | A1 | 11/2011 | Kugler et al. |
| 2012/0053485 | A1 | 3/2012 | Bloom |
| 2012/0095485 | A1 | 4/2012 | Cully et al. |
| 2012/0283571 | A1 | 11/2012 | Nita |
| 2012/0283761 | A1 | 11/2012 | Rosenthal et al. |
| 2012/0323220 | A1 | 12/2012 | Mackay, II et al. |
| 2012/0323251 | A1 | 12/2012 | Kugler et al. |
| 2012/0323269 | A1 | 12/2012 | Rottenberg et al. |
| 2013/0006167 | A1 | 1/2013 | Alvarez |
| 2013/0006173 | A1* | 1/2013 | Alvarez ............ A61M 25/0194 604/95.05 |
| 2013/0006282 | A1 | 1/2013 | Wilkinson |
| 2013/0072957 | A1 | 3/2013 | Anderson |

(56) References Cited

U.S. PATENT DOCUMENTS

| | | |
|---|---|---|
| 2013/0103070 A1 | 4/2013 | Kugler et al. |
| 2013/0116622 A1 | 5/2013 | Takagi |
| 2013/0150880 A1 | 6/2013 | Anderson |
| 2013/0158519 A1 | 6/2013 | Boutilette et al. |
| 2013/0245430 A1 | 9/2013 | Selmon et al. |
| 2013/0261545 A1 | 10/2013 | Osypka |
| 2013/0296907 A1 | 11/2013 | Robinson et al. |
| 2013/0304108 A1 | 11/2013 | Weber et al. |
| 2013/0310868 A1 | 11/2013 | Kuglar et al. |
| 2013/0317528 A1 | 11/2013 | Anderson et al. |
| 2014/0018732 A1 | 1/2014 | Bagaoisan et al. |
| 2014/0142607 A1* | 5/2014 | Cage ............... A61M 25/0054 606/185 |
| 2014/0275983 A1 | 9/2014 | Piccagli |
| 2015/0174371 A1 | 6/2015 | Schaeffer et al. |

FOREIGN PATENT DOCUMENTS

| | | |
|---|---|---|
| JP | 2008538190 | 10/2008 |
| JP | 2010512971 | 4/2010 |
| JP | 2011510795 | 4/2011 |
| WO | WO95/24236 | 9/1995 |
| WO | WO2006105244 | 10/2006 |
| WO | WO2008120209 | 10/2008 |
| WO | WO2009/100129 | 8/2009 |
| WO | WO2009144561 | 12/2009 |
| WO | WO2013003757 | 1/2013 |
| WO | 2013043592 A1 | 3/2013 |
| WO | WO2013164825 | 11/2013 |
| WO | WO2014039096 | 3/2014 |

OTHER PUBLICATIONS

U.S. Appl. No. 14/058,444, filed Oct. 21, 2013, Silvestro.
Shin et al. "Limitations of the Outback LTD re-entry device in femoropopliteal chronic total occlusions." Journal of Vascular Surgery, vol. 53, 5; 2010.
A. Bolia "Subintimial Angioplasty, the Way Forward" Acta chir belg, 2004, 104, 547-554.
Karkos et al. "Subintimal Recanalization of the Femoropopliteal Segment to Promote Healing of an Ulcerated Below-Knee Amputation Stump" J Endovasc Ther 2006;13:420-423.
Glasby et al. "Subintimal Angioplasty" Review, pp. 12-16, 2008.
JP2017-508556, Japanese Office Action dated Apr. 4, 2019, 3pgs.

* cited by examiner

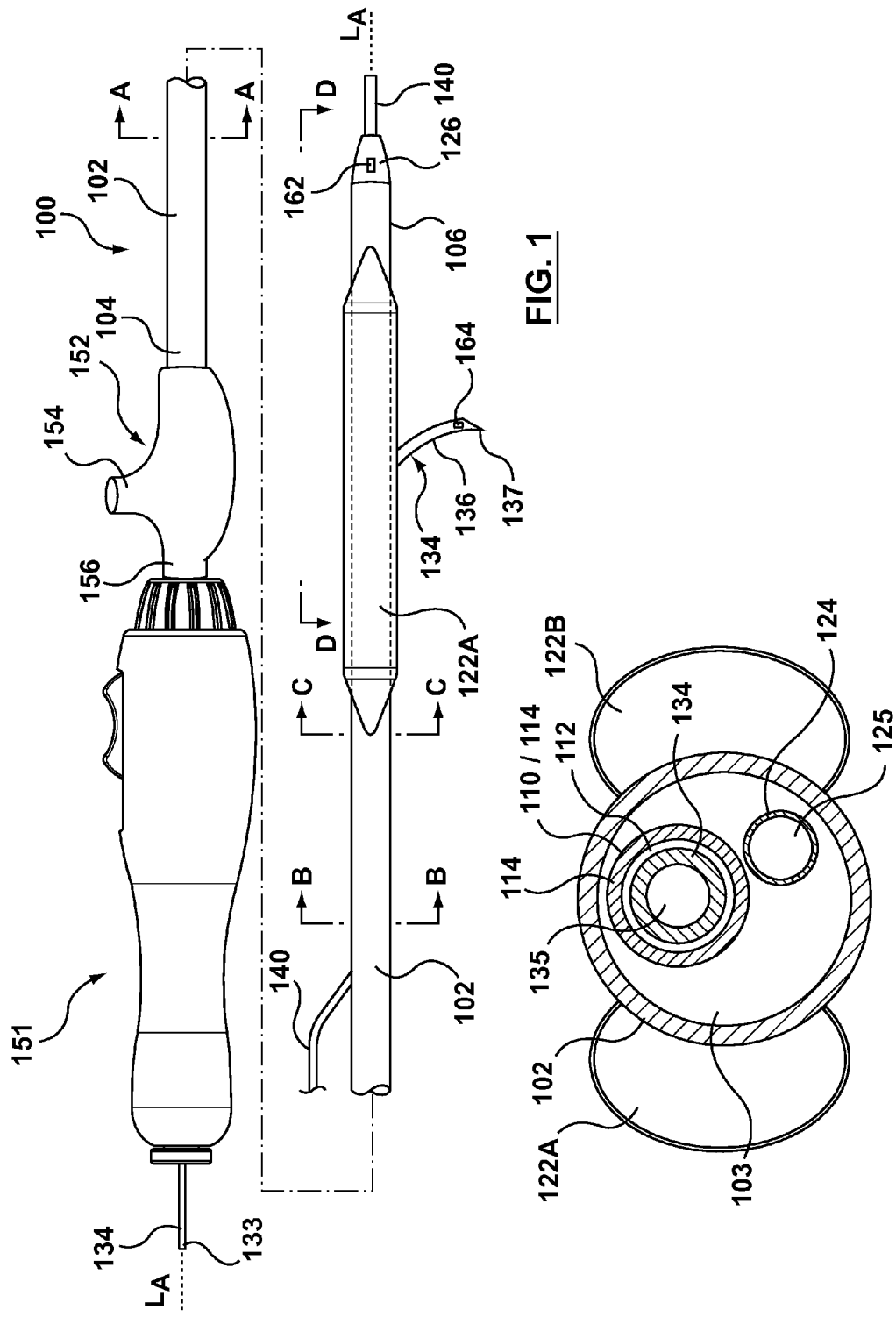

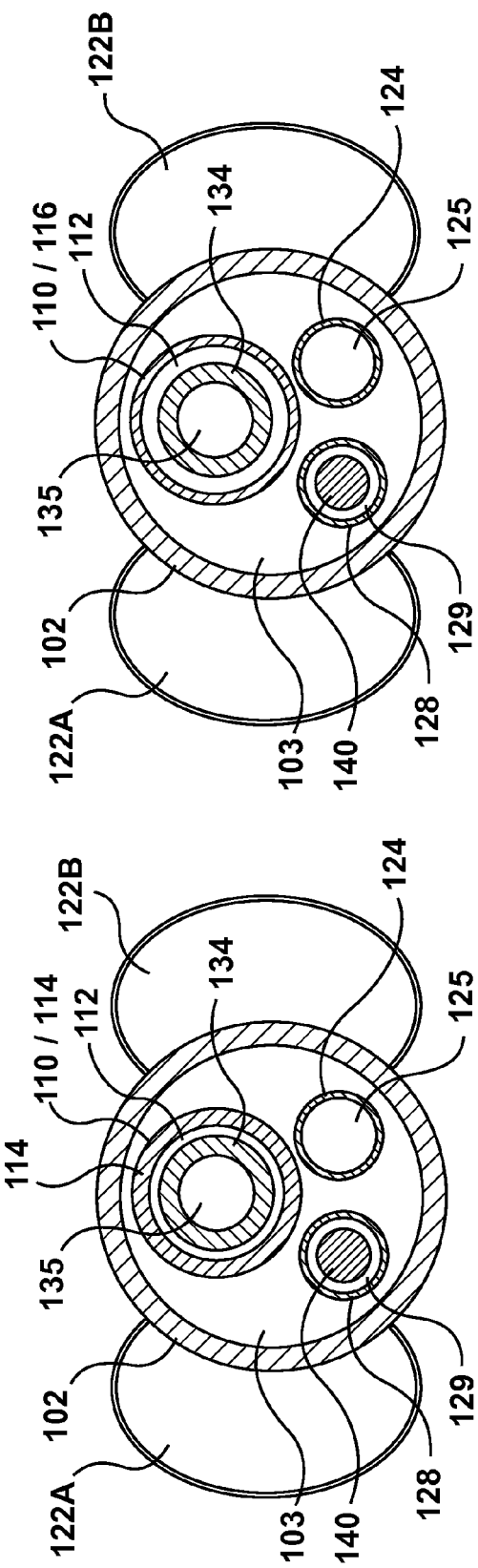

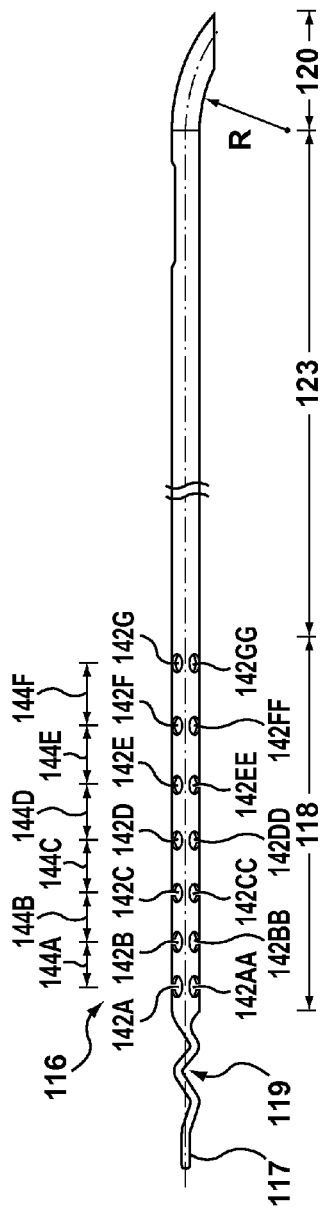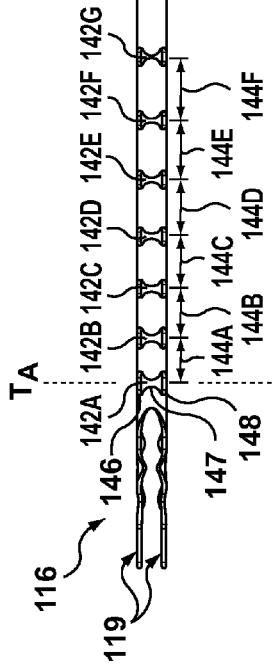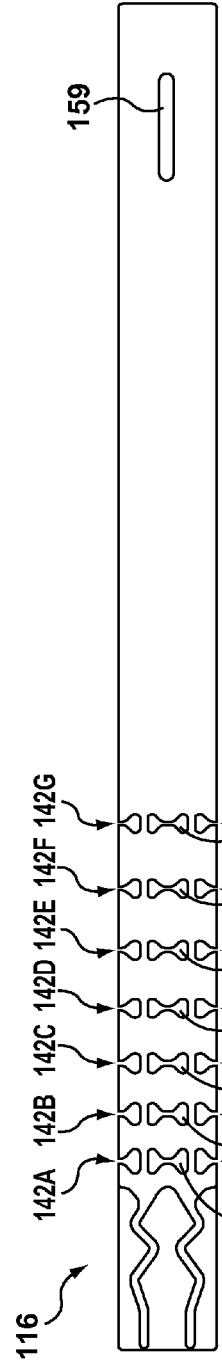
FIG. 6
FIG. 7
FIG. 8

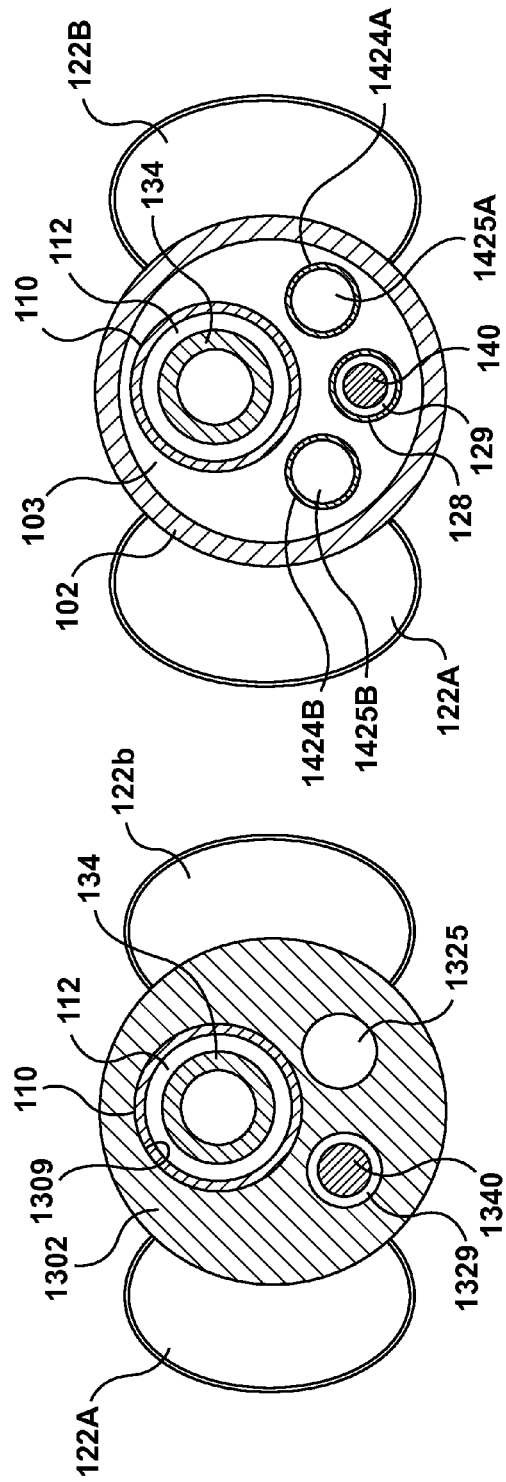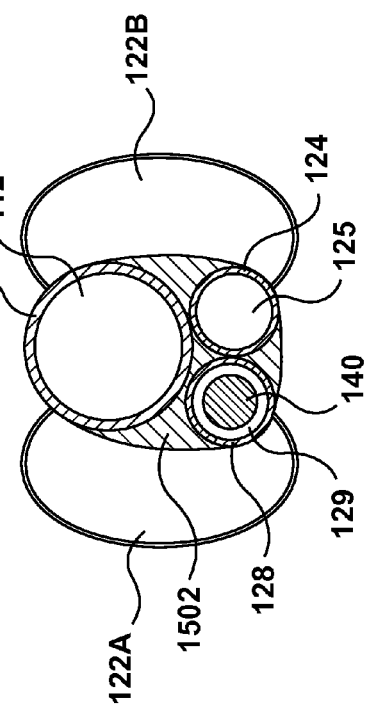

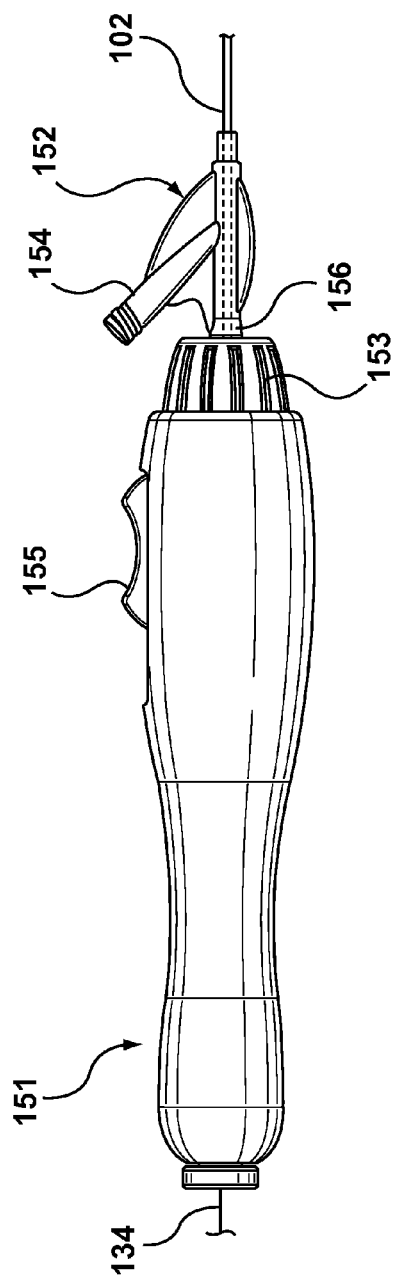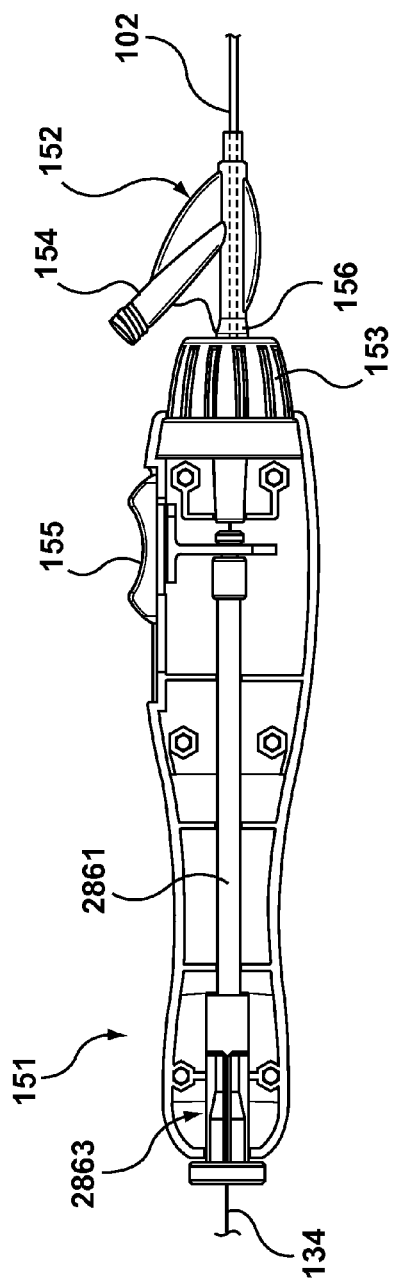

OCCLUSION BYPASSING APPARATUS WITH VARYING FLEXIBILITY AND METHODS FOR BYPASSING AN OCCLUSION IN A BLOOD VESSEL

FIELD OF THE INVENTION

The invention relates generally to an occlusion bypassing apparatus and methods of using the apparatus for subintimally bypassing a blockage in a blood vessel such as a chronic total occlusion and reentering the true lumen of the blood vessel beyond the blockage.

BACKGROUND OF THE INVENTION

Cardiovascular disease, including atherosclerosis, is a serious ailment for many people that may in some cases lead to death. One method for treating atherosclerosis and other forms of arterial lumen narrowing is percutaneous transluminal angioplasty, commonly referred to as "angioplasty" or "PTA," or "PTCA" when performed in the coronary arteries. The objective in angioplasty is to restore adequate blood flow through the affected artery, which may be accomplished by inflating a balloon of a balloon catheter within the narrowed lumen of the artery to dilate the vessel.

The anatomy of arteries varies widely from patient to patient. Often a patient's arteries are irregularly shaped, highly tortuous and very narrow. The tortuous configuration of the arteries may present difficulties to a clinician in advancement of the balloon catheter to a treatment site. In addition, in some instances, the extent to which the lumen is narrowed at the treatment site is so severe that the lumen is completely or nearly completely obstructed, which may be described as a total occlusion. Total or near-total occlusions in arteries can prevent all or nearly all of the blood flow through the affected arteries. If the occlusion has been established for a long period of time, the lesion may be referred to as a chronic total occlusion or CTO. Chronic total occlusions can occur in coronary as well as peripheral arteries. Chronic total occlusions are often characterized by extensive plaque formation and typically include a fibrous cap surrounding softer plaque material. This fibrous cap may present a surface that is difficult to penetrate with a conventional medical guidewire.

A number of devices have been developed and/or used for the percutaneous interventional treatment of CTOs, such as stiffer guidewires, low-profile balloons, laser light emitting wires, atherectomy devices, drills, drug eluting stents, and re-entry catheters. The factor that is most determinative of whether the physician can successfully recannalize a CTO is the physician's ability to advance a suitable guidewire from a position within the true lumen of the artery proximal to the CTO lesion, across the CTO lesion, i.e., either through the lesion or around it, and then back into the true lumen of the artery at a location distal to the CTO lesion.

In some cases, such as where the artery is totally occluded by hard, calcified atherosclerotic plaque, the guidewire may tend to deviate to one side and penetrate through the intima of the artery, thereby creating a neo-lumen called a "subintimal tract" i.e., a penetration tract formed within the wall of the artery between the intima and adventitia. In these cases, the distal end of the guidewire may be advanced to a position distal to the lesion but remains trapped within the subintimal tract. In such instances, it is then necessary to divert or steer the guidewire from the subintimal tract back into the true lumen of the artery at a location distal to the CTO lesion. The process of manipulating the guidewire to reenter the artery lumen is often difficult and solutions have been proposed utilizing various means for dealing with such a problem.

A number of catheter-based devices have been heretofore useable to redirect subintimally trapped guidewires back into the true lumen of the artery. Included among these are a variety of catheters having laterally deployable cannulae, i.e., hollow needles. For example, some catheter systems utilize a penetrator or needle that, thanks to the presence of an on-board imaging system (IVUS), exits through a side exit port of the catheter to puncture the intimal layer distal of the CTO to re-enter the true lumen of the vessel. A second guidewire is then passed through the laterally deployed needle and is advanced into the true lumen of the artery. However, a need in the art still exists for other medical catheters or systems that consistently and reliably direct subintimally advanced guidewires back into the true lumen of the artery for the treatment of a CTO.

BRIEF SUMMARY OF THE INVENTION

Embodiments hereof are directed to an apparatus for bypassing an occlusion in a blood vessel. The apparatus includes an outer shaft component, an inner shaft component, and a needle component. The outer shaft component has a side port proximal to a distal end thereof. The inner shaft component is disposed within the outer shaft component and defines a continuous lumen there-through. The inner shaft component has a body portion that extends substantially parallel with a longitudinal axis of the apparatus and a needle housing distally extending from a distal end of the body portion. The needle housing includes a curved distal portion that bends from the longitudinal axis of the apparatus and terminates at the side port of the outer shaft component and a transition portion positioned between the body portion of the inner shaft component and the distal portion of the needle housing. The transition portion has a variable flexibility along its length that decreases in a distal direction. The needle component is configured to be slidably disposed within the continuous lumen of the inner shaft component and removable therefrom. The needle component has a curved distal end with a bend that corresponds with, matches or is the same as the bend of the curved distal portion of the needle housing.

In another embodiment hereof, the apparatus includes an outer shaft component, an inner shaft component, and a needle component. The outer shaft component has a side port proximal to a distal end thereof. The inner shaft component is disposed within the outer shaft component and defines a continuous lumen there-through. The inner shaft component has a body portion that extends substantially parallel with a longitudinal axis of the apparatus and a needle housing distally extending from a distal end of the body portion. The needle housing includes a curved distal portion that bends from the longitudinal axis of the apparatus and terminates at the side port of the outer shaft component and a transition portion positioned between the body portion of the inner shaft component and the distal portion of the needle housing. The apparatus is more flexible along the body portion of the inner shaft component than along the distal portion of the needle housing and the transition portion has a variable flexibility along its length that decreases in a distal direction. A needle component is configured to be slidably disposed within the continuous lumen of the inner shaft component and removable therefrom. The needle component has a curved distal end. In a first configuration of the apparatus, the curved distal end of the needle component is held in a straightened form within the needle housing of the inner shaft component. In a second configuration of the apparatus the curved distal end of the needle component extends from the side port of the outer shaft component and bends from the longitudinal axis of the apparatus.

In another embodiment hereof, the apparatus for bypassing an occlusion in a blood vessel includes an outer shaft component, an inner shaft component, and a needle component. The outer shaft component has a side port proximal to a distal end thereof and at least one balloon disposed proximal to the distal end thereof. The outer shaft component defines an inflation lumen in fluid communication with the at least one balloon and a guidewire lumen extending at least along a distal portion thereof. The inner shaft component is disposed within the outer shaft component and defines a continuous lumen there-through. The inner shaft component has a body portion that extends substantially parallel with a longitudinal axis of the apparatus and a needle housing distally extending from a distal end of the body portion. The needle housing includes a curved distal portion that bends from the longitudinal axis of the apparatus and terminates at the side port of the outer shaft component and a transition portion positioned between the body portion of the inner shaft component and the distal portion of the needle housing. The transition portion has a variable flexibility along its length that decreases in a distal direction. A needle component is configured to be slidably disposed within the continuous lumen of the inner shaft component and removable therefrom. The needle component has a curved distal end with a bend that corresponds with, matches or is the same as the bend of the curved distal portion of the needle housing.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1 is a side view of an occlusion bypassing apparatus according to an embodiment hereof, wherein the occlusion bypassing apparatus is shown advanced over a guidewire in a deployed configuration in which a needle component thereof is extended through a side port of an outer shaft component and lateral balloons of the occlusion bypassing apparatus are expanded.

FIG. 1A is a cross-sectional view of the occlusion bypassing apparatus of FIG. 1 taken along line A-A thereof, wherein line A-A is located proximal to a proximal guidewire port of the occlusion bypassing apparatus.

FIG. 1B is a cross-sectional view of the occlusion bypassing apparatus of FIG. 1 taken along line B-B thereof, wherein line B-B is located distal to a proximal guidewire port of the occlusion bypassing apparatus and along a body portion of an inner shaft component of the occlusion bypassing apparatus.

FIG. 1C is a cross-sectional view of the occlusion bypassing apparatus of FIG. 1 taken along line C-C thereof, wherein line C-C is located distal to a proximal guidewire port of the occlusion bypassing apparatus and along a needle housing of an inner shaft component of the occlusion bypassing apparatus.

FIG. 6 is a side view of the needle housing of the inner shaft component of FIG. 5, wherein the needle housing is removed from the inner shaft component for illustrative purposes only.

FIG. 7 is a top view of the needle housing of FIG. 6.

FIG. 8 is a laser-cut pattern of the needle housing of FIG. 6, wherein the laser-cut pattern is laid out flat for illustrative purposes only.

FIG. 13 is a cross-sectional view of an alternative embodiment of an occlusion bypassing apparatus, wherein the lumens of the outer shaft component are formed via multi-lumen extrusion.

FIG. 14 is a cross-sectional view of an alternative embodiment of an occlusion bypassing apparatus, wherein the outer shaft component includes two inflation lumens for separately delivering inflation fluid to two lateral balloons.

FIG. 15 is a cross-sectional view of an alternative embodiment of an occlusion bypassing apparatus, wherein a guidewire tube and an inflation tube are bonded to an outer surface of the inner shaft component.

FIG. 27 is a side view of the handle of the occlusion bypassing apparatus of FIG. 1.

FIG. 28 is a sectional view of the handle of the occlusion bypassing apparatus of FIG. 1, taken along line X-X of FIG. 26.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of the invention is in the context of treatment of blood vessels such as smaller diameter peripheral or coronary arteries, the invention may also be used in any other body passageways where it is deemed useful. Although the description of the invention generally refers to a system and method of bypassing a vessel blockage in a proximal-to-distal direction, i.e. antegrade or with the blood flow, the invention may be used equally well to bypass a vessel blockage in a distal-to-proximal direction, i.e. retrograde or against the blood flow, if access is available from that direction. In other terms, the system and method described herein may be considered to bypass a vessel blockage from a near side of the blockage to a far side of the blockage. Furthermore, there is no intention to be bound by any expressed or implied theory presented in the preceding technical field, background, brief summary or the following detailed description.

Figure 1D:
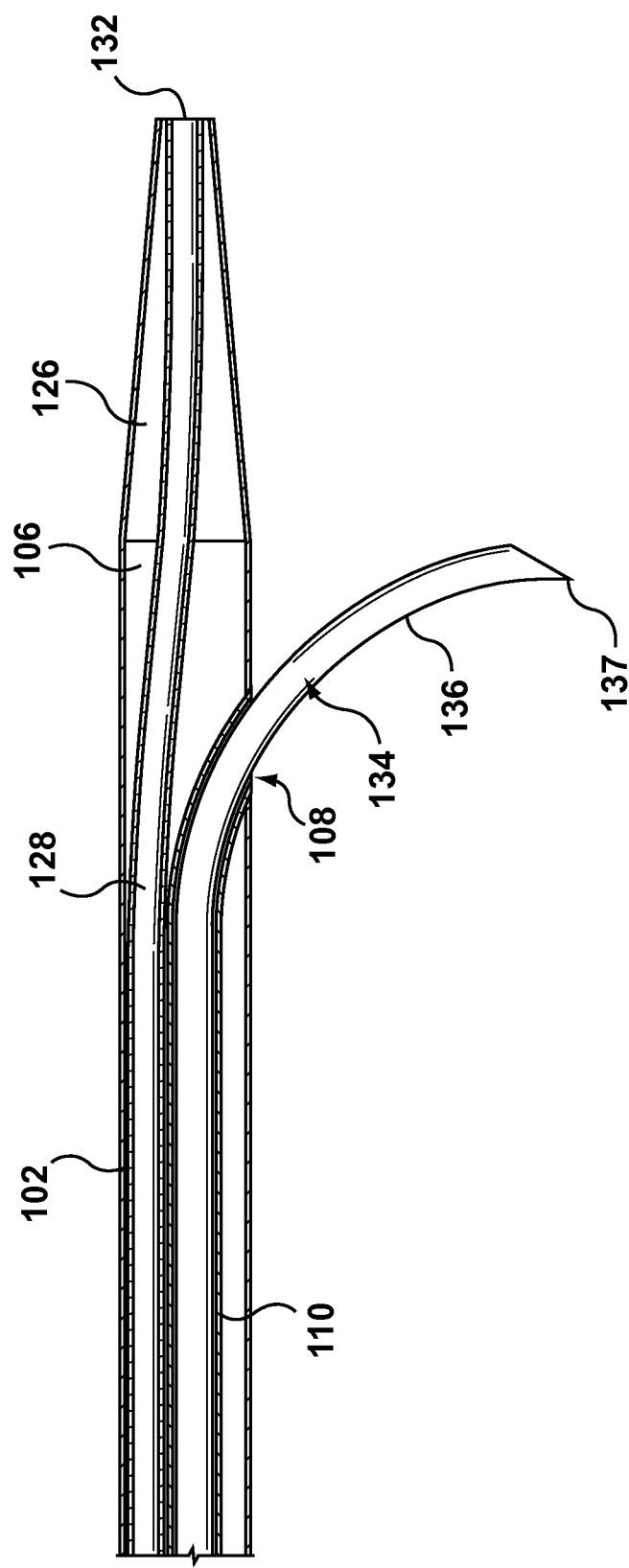
FIG. 1D is a partial longitudinal sectional view of the occlusion bypassing apparatus of FIG. 1 taken along line D-D thereof.
Figure 2:
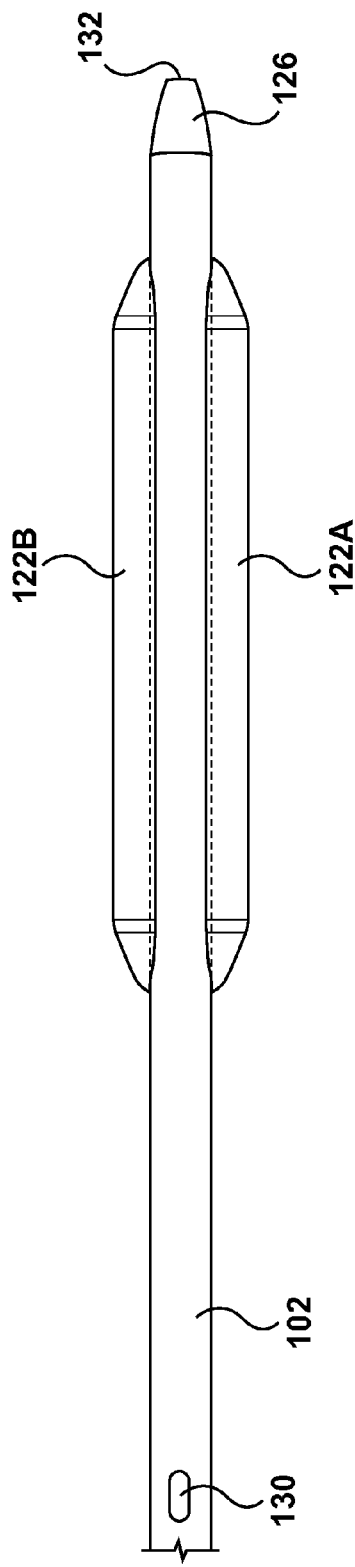
FIG. 2 is a top view of a distal portion of the occlusion bypassing apparatus of FIG. 1 with the guidewire removed.
Figure 3:
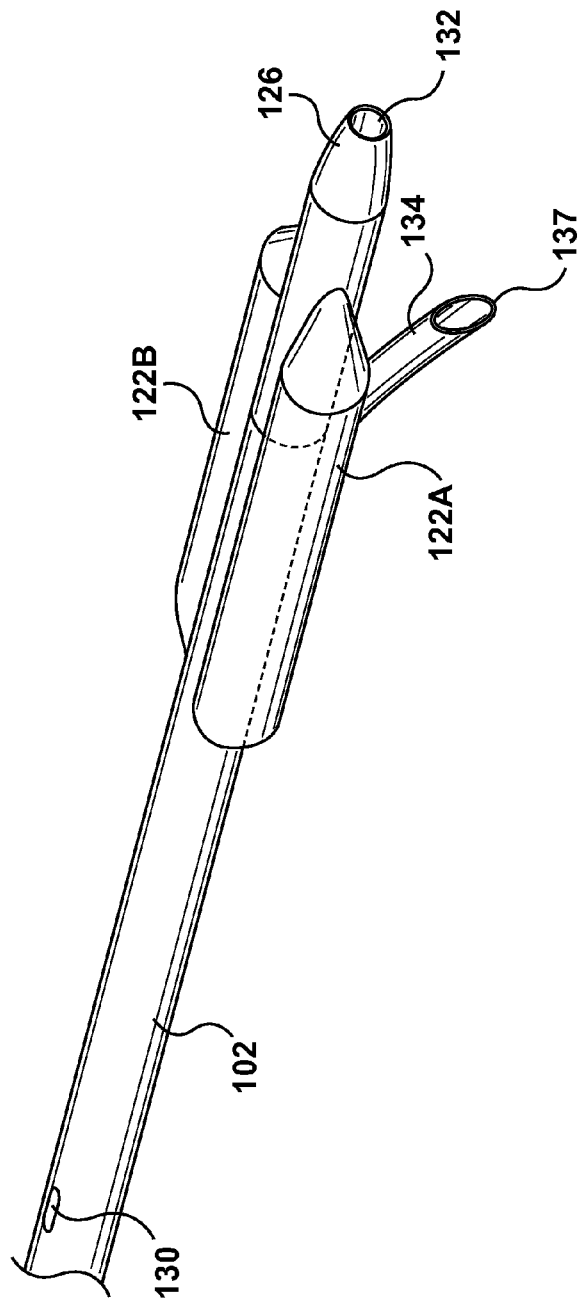
FIG. 3 is a perspective view of a distal portion of the occlusion bypassing apparatus of FIG. 1 with the guidewire removed.

Embodiments hereof relate to a system and method for re-entering the true lumen of a vessel after subintimally bypassing an occlusion in a blood vessel such as a chronic total occlusion (CTO) of an artery. FIG. 1 illustrates a side view of an occlusion bypassing apparatus 100 in its deployed configuration, with FIG. 1A, FIG. 1B, FIG. 1C being cross-sectional views which are taken at different longitudinal locations along occlusion bypassing apparatus 100 and FIG. 1D being a sectional view taken along line D-D of FIG. 1. FIG. 2 and FIG. 3 are top and perspective views, respectively, of a distal portion of occlusion bypassing apparatus 100. Occlusion bypassing apparatus 100 includes an outer shaft component 102 with first and second lateral balloons 122A, 122B for stabilization or anchoring thereof, an inner shaft component 110 disposed within outer shaft component 102, and a needle component 134 slidably and removably disposed within a continuous lumen 112 of inner shaft component 110. As used herein, "slidably" denotes back and forth movement in a longitudinal direction. As will be explained in more detail herein, inner shaft component 110 and thus occlusion bypassing apparatus 100 has a variable flexibility along its length for accommodating needle component 134. While stabilized or anchored within a subintimal space of a vessel, a curved distal end 136 of needle component 134 is advanced out of a side port 108 (see FIG. 1D) of outer shaft component 102 towards the true lumen of the vessel. In FIGS. 1-3, curved distal end 136 of needle component 134 is shown extended from side port 108 of outer shaft component 102 in a deployed configuration that is suitable for puncturing the vessel wall to gain access to the true lumen.

Outer shaft component 102 is a tubular or cylindrical element that defines a lumen 103 (see FIG. 1A) that extends from a proximal end 104 to distal end 106 of the outer shaft component and has first lateral balloon 122A and second lateral balloon 122B mounted on a distal portion thereof. A flexible distal tip 126 is coupled to distal end 106 of outer shaft component 102. As best shown on the top view of FIG. 2 and the perspective view of FIG. 3, lateral balloons 122A, 122B are disposed in parallel on opposing sides of outer shaft component 102. Side port 108 of outer shaft component 102, through which needle component 134 is advanced, is proximal to distal end 106 thereof. In an embodiment, side port 108 is disposed midway along the length of lateral balloons 122A, 122B in order to optimize the stabilization function of the balloons. Although shown with dual lateral balloons, embodiments hereof may utilize other balloon configurations for stabilization of the occlusion bypassing apparatus, including but not limited to a single cylindrical balloon that circumferentially surrounds the outer shaft component. If a single cylindrical balloon is utilized, the side port of the outer shaft component may be moved slightly proximal of the balloon so that the balloon does not surround the side port. Proximal end 104 of outer shaft component 102 extends out of the patient and is coupled to a first hub 152. An inflation shaft or tube 124 defining an inflation lumen 125 extends through lumen 103 of outer shaft component 102. Inflation lumen 125 is in fluid communication with first lateral balloon 122A and second lateral balloon 122B to allow inflation fluid received through first hub 152 to be concurrently delivered to both of the lateral balloons. As would be understood by one of ordinary skill in the art of balloon catheter design, hub 152 includes a hemostatic valve 156 to accommodate insertion of occlusion bypassing apparatus 100 and a luer hub 154 or other type of fitting that may be connected to a source of inflation fluid (not shown) and may be of another construction or configuration without departing from the scope of the present invention. When inflated, lateral balloons 122A, 122B anchor outer shaft component 102 within the anatomy, more particularly within the subintimal space of the vessel wall when utilized in the treatment of a CTO, so as to provide stability to occlusion bypassing apparatus 100.

In addition to inflation shaft 124, a relatively short guidewire shaft or tube 128 defining a guidewire lumen 129 extends through a distal portion of lumen 103 of outer shaft component 102 in a so-called rapid-exchange configuration for accommodating a guidewire 140. More particularly, guidewire shaft 128 extends from a proximal guidewire port 130 (see FIGS. 2 and 3) to a distal guidewire port 132 (see FIGS. 2 and 3). Guidewire 140 is omitted from FIG. 2 and FIG. 3 in order to clearly show proximal and distal guidewire ports 130, 132, respectively. With reference to the cross-sectional views of FIG. 1A, FIG. 1B, FIG. 1C, which are taken at different longitudinal locations along occlusion bypassing apparatus 100, guidewire shaft 128 extends within outer shaft component 102 in longitudinal locations distal to proximal guidewire port 130, i.e., as shown in FIG. 1B and FIG. 1C, but does not extend within outer shaft component proximal to proximal guidewire port 130, i.e., as shown in FIG. 1A. Guidewire shaft 128 may have a length between 5 cm and 20 cm. In an embodiment, outer shaft component 102 may be sized to be used with a 5F introducer sheath with guidewire lumen 129 being sized to accommodate a guidewire having an outer diameter of 0.014 inch.

Outer shaft component 102, as well as inflation shaft 124 and guidewire shaft 128, may be formed of one or more polymeric materials, non-exhaustive examples of which include polyethylene, polyethylene block amide copolymer (PEBA), polyamide and/or combinations thereof, either laminated, blended or co-extruded. Optionally, outer shaft component 102 or some portion thereof may be formed as a composite having a reinforcement layer incorporated within a polymeric body in order to enhance strength and/or flexibility and/or torquability. Suitable reinforcement layers include braiding, wire mesh layers, embedded axial wires, embedded helical or circumferential wires, hypotubes, and the like. In one embodiment, for example, at least a proximal portion of outer shaft component 102 may be formed from a reinforced polymeric tube.

Figure 5:
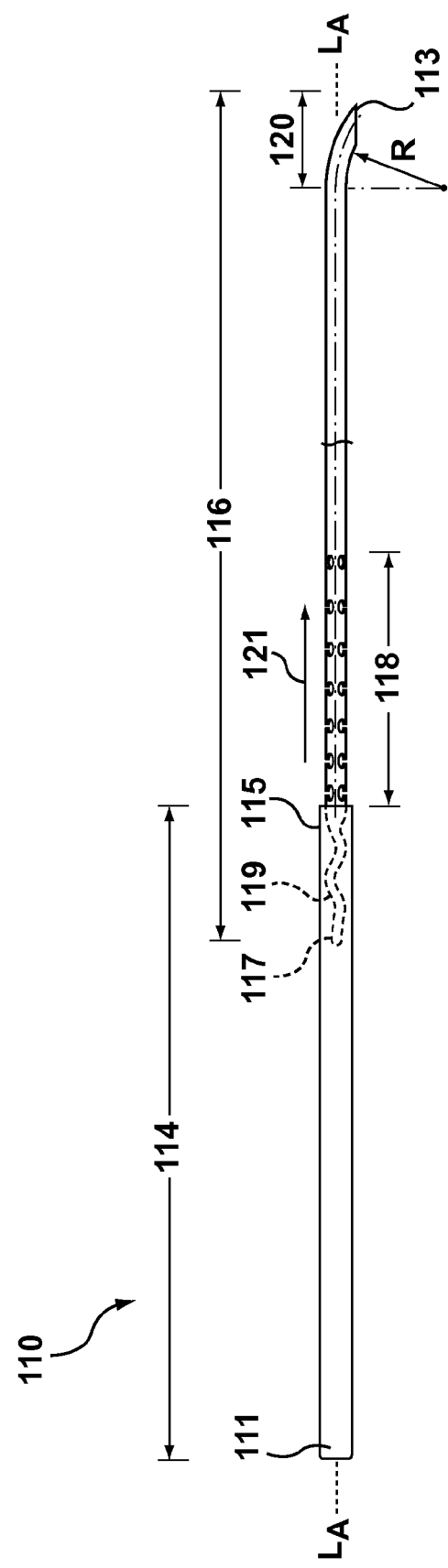
FIG. 5 is a side view of the inner shaft component of the occlusion bypassing apparatus of FIG. 1, wherein the inner shaft component is removed from the occlusion bypassing apparatus for illustrative purposes only.

As previously stated, inner shaft component 110 and thus occlusion bypassing apparatus 100 has a variable flexibility along its length for accommodating needle component 134. More particularly, inner shaft component 110 is a tubular or cylindrical element disposed within lumen 103 of outer shaft component 102. As best shown in FIG. 5 which illustrates inner shaft component 110 removed from occlusion bypassing apparatus 100 for illustrative purposes only, inner shaft component 110 includes a first or body portion 114 that extends substantially parallel with a longitudinal axis $L_A$ of occlusion bypassing apparatus 100 and a needle housing 116 distally extending from a distal end 115 of the body portion. As shown in FIG. 5, a proximal end 117 of needle housing 116 is joined or attached to distal end 115 of body portion 114 in an overlapping manner. Body portion 114 and needle housing 116 collectively define continuous lumen 112 (see FIG. 1A) that extends from a proximal end 111 to a distal end 113 of inner shaft component 110 for accommodating needle component 134. FIG. 1B is a cross-sectional view that shows needle component 134 within body portion 114 of inner shaft component 110, while FIG. 1C is a cross-sectional view (which is taken at a more distal longitudinal location along occlusion bypassing apparatus 100) that shows needle component 134 within needle component 116 of inner shaft component 110.

In accordance with embodiments hereof, body portion 114 is a tubular or cylindrical shaft segment having a first flexibility while needle housing 116 is a tubular or cylindrical shaft segment having a second flexibility so that the needle housing 116 is less flexible or stiffer than body portion 114. In accordance with an embodiment hereof, body portion 114 may be an elongate polymeric tube with a reinforcing mesh or wire layer being incorporated within the polymeric material and needle housing 116 may be a metallic tube of a relatively shorter length than the length of body portion 114. Typically, the needle housing length is about 2-5% of the body portion length. For example, body portion 114 may be a polymeric tube formed of a flexible polymeric material, non-exhaustive examples of which include polyethylene, polyethylene block amide copolymer (PEBA), polyamide and/or combinations thereof, having a braiding or wire mesh layer incorporated within a wall thereof to enhance the column strength thereof. Body portion 114 ensures that inner shaft component 110, and thus occlusion bypassing apparatus 100, has the required flexibility and torquability necessary for in situ delivery. Needle housing 116 is preferably formed from a shape memory material such as nitinol to ensure high flexibility of occlusion bypassing apparatus 100 during advancement through the vasculature. Alternatively, needle housing 116 may be formed from a metallic resilient material such as steel or spring temper stainless steel.

Needle housing 116 includes a curved distal portion 120 that bends from the longitudinal axis $L_A$ of occlusion bypassing apparatus 100. Curved distal portion 120 includes a pre-formed or pre-shaped bend or curve. A heat or thermal treatment of the selected material of needle housing 116 may be used to set the shape of curved distal portion 120. More particularly, as shown in FIG. 5, curved distal portion 120 extends, bends, or otherwise curves in a circular path while the remaining length of needle housing 116 is straight and extends parallel to the longitudinal axis $L_A$ of occlusion bypassing apparatus 100. In an embodiment hereof, curved distal portion 120 extends in a circular path and forms a portion of a circle having a radius R. In an embodiment hereof, radius R is 5 mm. Typically, radius R is in the range from 4 mm to 8 mm. As best shown in the sectional view of FIG. 4, distal portion 120 of needle housing 116 terminates at side port 108 of outer shaft component 102. The curved distal portion 120 of needle housing 116 functions as a guide to direct needle component 134 through side port 108 such that needle component 134 exits occlusion bypassing apparatus 100 in a stable configuration at a desired orientation for re-entry into a true lumen.

In order to smooth or bridge the transition between flexible body portion 114 and relatively stiffer or less flexible needle housing 116, needle housing 116 includes a transition portion 118. Transition portion 118 is disposed distal to distal end 115 of body portion 114 and proximal to distal portion 120 of needle housing 116. Transition portion 118 has a variable flexibility along its length that decreases in a distal direction as indicated by directional arrow 121 (see FIG. 5). Since the flexibility of transition portion 118 decreases in a distal direction, the transition portion allows for a gradual modulation of the flexibility between the flexible body portion 114 (located proximal to transition portion 118) and relatively less flexible, or rigid, needle housing 116 (located distal to transition portion 118). The flexibility of occlusion bypassing apparatus 100 corresponds to the flexibility of inner shaft component 110, with occlusion bypassing apparatus 100 being more flexible along body portion 114 of inner shaft component 110 and less flexible along needle housing 116 of inner shaft component 110. Transition portion 118 similarly will provide occlusion bypassing apparatus 100 with a variable flexibility along its length that decreases in a distal direction.

Needle housing 116 will now be discussed in more detail with reference to FIGS. 6-8. FIG. 6 and FIG. 7 are side and top views, respectively, of needle housing 116 removed from inner shaft component 110 for illustrative purposes only, while FIG. 8 is a laser cut pattern laid flat for illustrative purposes that may be used in the manufacture of the needle housing. As shown in FIGS. 6-7, proximal end 117 of needle housing 116 includes two tabs or extensions 119 that proximally extend from transition portion 118. As best shown on the top view of FIG. 7, tabs 119 are disposed in parallel on opposing sides of needle housing 116. Tabs 119 may have a sinusoidal or wavy configuration in the longitudinal direction. When body portion 114 and needle housing 116 are coupled together, tabs 119 extend or are embedded into the polymeric material of body portion 114. Tabs 119 provide a smooth junction between body portion 114 and needle housing 116.

In order to provide transition portion 118 of needle housing 116 with varying flexibility, transition portion 118 includes a plurality of apertures 142A, 142AA, 142B, 142BB, 142C, 142CC, 142D, 142DD, 142E, 142EE, 142F, 142FF, 142G, 142GG, wherein pairs of apertures 142A and 142AA, apertures 142B and 142BB, etc. align with each other along a respective transverse axis $T_A$ (shown in FIG. 7) of needle housing 116. Each aperture is a cut-out portion or window that increases the flexibility of transition portion 118 as compared to the remaining length of needle housing 118, i.e., straightening portion 123 of needle housing 116 and curved distal portion 120 which have no apertures or cut-out portions formed therein. As used herein, any respective pair of aligned apertures may be referred to singularly or collectively as a pair or pairs of aligned apertures 142. Although shown with seven pairs of aligned apertures 142, a greater or lesser number of pairs of aligned apertures 142 may be used to provide transition portion 118 with varying flexibility. As best shown in FIG. 8, each aperture in a pair of aligned apertures 142 has an hourglass shape and is disposed from the other aperture of the pair on an opposite side of the perimeter or outer surface of needle housing 116 so as to be diametrically opposed thereto. In order to provide transition portion 118 with varying flexibility along its length that decreases in a distal direction, the pitch or spacing between adjacent pairs of aligned apertures increases in a distal direction. More particularly, each pair of aligned apertures 142 are spaced apart by a series of distances 144A, 144B, 144C, 144D, 144E, 144F. The distance or spacing 144A between aligned apertures 142A, 142AA and aligned apertures 142B, 142BB is less than the distance or spacing 144B between aligned apertures 142B, 142BB and aligned apertures 142C, 142CC. The distance or spacing between adjacent pairs of aligned apertures 142 continues to increase such that distance or spacing 144F between the most distal apertures, aligned apertures 142F, 142FF and aligned apertures 142G, 142GG, is the greatest. Since a greater amount of metallic material extends between consecutive pairs of aligned apertures 142, gradually increasing the pitch or spacing between axially adjacent pairs of aligned apertures 142 in the distal direction results in a gradual decrease of flexibility in the distal direction.

In addition or in the alternative to varying the spacing between adjacent pairs of aligned apertures 142, in another embodiment the size or area of adjacent pairs of aligned apertures 142 may be varied in order to result in a gradual decrease of flexibility along the length of transition portion 118 in the distal direction. More particularly, in the embodiment of FIGS. 6-8, each hourglass or barbell shaped aperture may be described to have a top region 146, a bottom region 148, and a narrowed waist region 147 extending between top and bottom regions 146, 148 as best shown in FIG. 7. In order to provide transition portion 118 with varying flexibility along its length that decreases in a distal direction, a width of top regions 146, bottom regions 148, and/or waist regions 147 of a pair of aligned apertures 142 may be decreased relative to a width of top regions 146, bottom regions 148, and/or waist regions 147 of a pair of adjacent aligned apertures 142 proximal thereof. More particularly, the width of top region 146, bottom region 148, and/or waist region 147 of the pair of aligned apertures 142A, 142AA may be greater than the width of top region 146, bottom region 148, and/or waist region 147 of the adjacent pair of aligned apertures 142B, 142BB. The widths continue to decrease such that the most distal pair of aligned apertures 142G, 142GG has the smallest or narrowest top region 146, bottom region 148, and/or waist region 147. Gradually decreasing the size of aligned apertures 142 in the distal direction results in a gradual decrease of flexibility in the distal direction. In the embodiment of FIGS. 6-8, each pair of aligned apertures 142 is shown with a decreased width or size relative to a pair of adjacent apertures 142 proximal thereof. However, in another embodiment hereof (not shown), only selected pairs of aligned apertures 142 may have a decreased width or size relative to a pair of adjacent apertures 142 proximal thereof.

Needle housing 116 may include a radiopaque marker 160 coupled thereto in order to visually monitor the position thereof. In order to couple marker 160 to needle housing 116 without increasing the profile of the needle housing, a portion of the tube that forms needle housing 116 may be removed and replaced with radiopaque marker 160, which has the same inner diameter and the same outer diameter as the tube that forms needle housing 116. Stated another way, an opening or hole 159 (see laser-cut pattern of FIG. 8) may be formed within needle housing 116 and marker 160 may be inserted therein such that marker 160 does not increase the profile of the needle housing. As shown in the top view of FIG. 7, in one embodiment, marker 160 is positioned on the "top" surface of needle housing 116 that opposes the distal exit of the needle housing. Further, marker 160 may be positioned along straightening portion 123 of needle housing 116, just proximal to curved distal portion 120. Marker 160 may be formed from any type of radiopaque material, including but not limited to Tantalum, Pt—Ir, and Gold. As described in more detail herein, occlusion bypassing apparatus 100 may include additional radiopaque markers in order to visually monitor the location and orientation of the apparatus in situ.

In addition to smoothing or bridging the transition between flexible body portion 114 and relatively stiffer or less flexible needle housing 116, transition portion 118 of needle housing 116 also functions to provide the needle housing with preferential bending. More particularly, the particular cut pattern of transition portion 118, i.e., a cut pattern having pairs of aligned apertures 142, allows for bending of inner shaft component 110, and thus occlusion bypassing apparatus 100, only along a vertical plane passing through the longitudinal axis of the apparatus but not in other directions. Stated another way, transition portion 118 allows for bending of occlusion bypassing apparatus 100 only along the plane of needle deployment. Such preferential bending provides preferential orientation of side port 108. More particularly, occlusion bypassing apparatus 100 is only permitted to bend in two possible directions, a first direction being towards a true lumen of a vessel and a second opposing direction. One or more radiopaque markers of occlusion bypassing apparatus 100, which are described in more detail herein, may be utilized to distinguish between the first and second directions and, if necessary, the orientation of the occlusion bypassing apparatus may be corrected by rotating the apparatus such that side port 108 is oriented towards the true lumen of the vessel.

Figure 9:
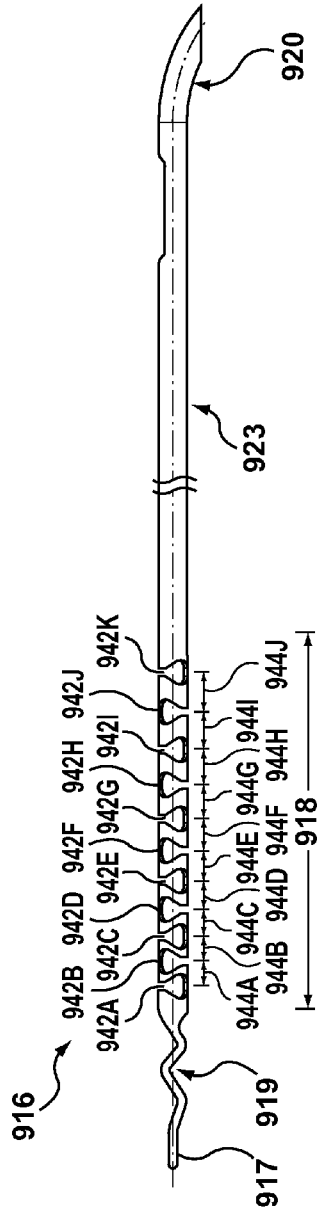
FIG. 9 is a side view of a needle housing according to another embodiment hereof, wherein the needle housing is removed from an inner shaft component for illustrative purposes only.
Figure 10:
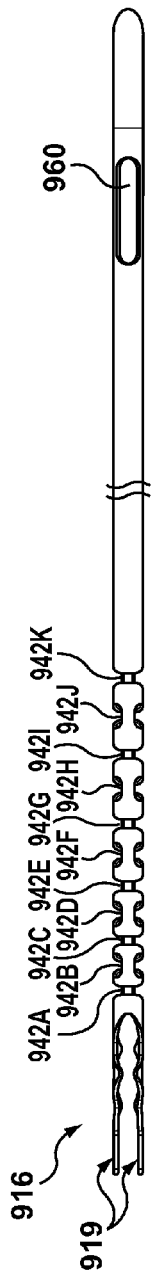
FIG. 10 is a top view of the needle housing of FIG. 9.
Figure 11:
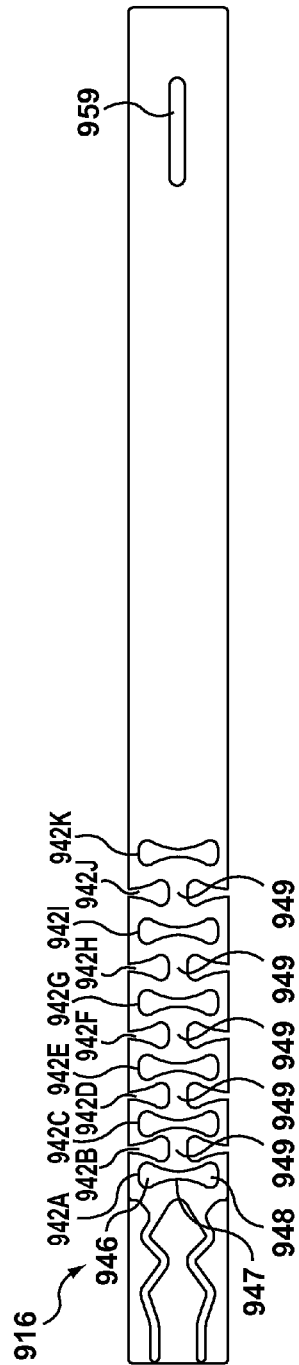
FIG. 11 is a laser-cut pattern of the needle housing of FIG. 9, wherein the laser-cut pattern is laid out flat for illustrative purposes only.

In another embodiment, the needle housing of the inner component may be formed with an alternative cut pattern in order to form the transition portion with variable flexibility. FIGS. 9-11 illustrate an alternate embodiment of a needle housing 916. FIGS. 9 and 10 are side and top views, respectively, of needle housing 916 removed from an inner shaft component for illustrative purposes only, while FIG. 11 is a laser cut pattern laid flat for illustrative purposes that may be used in the manufacture of the needle housing. Proximal end 917 of needle housing 916 includes two tabs or extensions 919 that proximally extend from a transition portion 918. Tabs 919 are similar to tabs 119 described above. In addition, needle housing 916 includes a curved distal portion 920 that is similar to curved distal portion 120 described above and a radiopaque marker 960 positioned within an opening or hole 959 (see laser-cut pattern of FIG. 11) similar to radiopaque marker 160 described above.

In order to provide transition portion 918 with varying flexibility, transition portion 918 includes a plurality of apertures or slots 942A, 942B, 942C, 942D, 942E, 942F, 942G, 942H, 942I, 942J, 942K herein collectively referred to as slots 942. Although shown with eleven slots 942, a greater or lesser number of slots may be used to provide transition portion 918 with varying flexibility. Slots 942 are cut-out portions or windows in needle housing 916 that increase the flexibility of transition portion 918 as compared to the remaining length of needle housing 916, i.e., straightening portion 923 of needle housing 916 which has no cut-out portions or slots formed therein and curved distal portion 920. As best shown in FIG. 11, each slot 942 has an hourglass shape that extends or partially wraps around the perimeter or outer surface of needle housing 916 and includes end regions 946, 948 with a waist region 947 therebetween, wherein respective end regions 946, 948 are separated by a bridge area 949. Adjacent hourglass-shaped slots 942 are made such that bridge area 949 (see FIG. 11) of a first slot 942 longitudinally aligns with a waist region 947 of a second, adjacent slot 942. Further, in order to provide transition portion 918 with flexibility that decreases along its length in a distal direction, the pitch or spacing between adjacent slots 942 increases in a distal direction. More particularly, slots 942 are spaced apart by a series of distances 944A, 944B, 944C, 944D, 944E, 944F, 944G, 944H, 944I, 944J, wherein the distance or spacing 944A between adjacent slots 942A, 942B is less than the distance or spacing 944B between adjacent slots 942B, 942C, and so on. In the embodiment of FIGS. 9-11, the distance or spacing between adjacent slots continues to gradually increase such that distance or spacing 944J between the most distal pair of adjacent slots 942J, 942K is the greatest. Since a greater amount of metallic material extends between consecutive slots, gradually increasing the pitch or spacing between adjacent slots 942 in the distal direction results in a gradual decrease of flexibility in the distal direction. In the embodiment of FIGS. 9-11, slots 942A, 942B, 942C, 942D, 942E, 942F, 942G, 942H, 942I, 942J, 942K each have the same size or area. However, in another embodiment hereof, the size or area of slots 942 may be varied in order to further vary the flexibility along the length of transition portion 918 as described with respect to transition portion 118 above. Similar to transition portion 118, transition portion 918 of needle housing 916 functions to provide the needle housing with preferential bending in the plane of the needle deployment.

Figure 25:
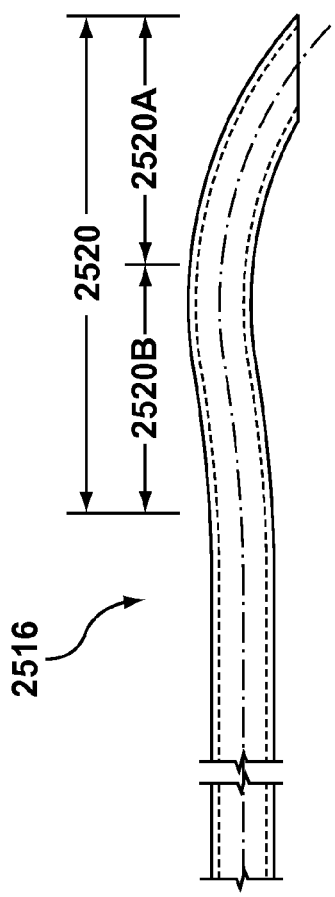
FIG. 25 illustrates a distal portion of a needle housing according to another embodiment hereof, wherein the needle housing includes two curved portions along its length.
Figure 26:
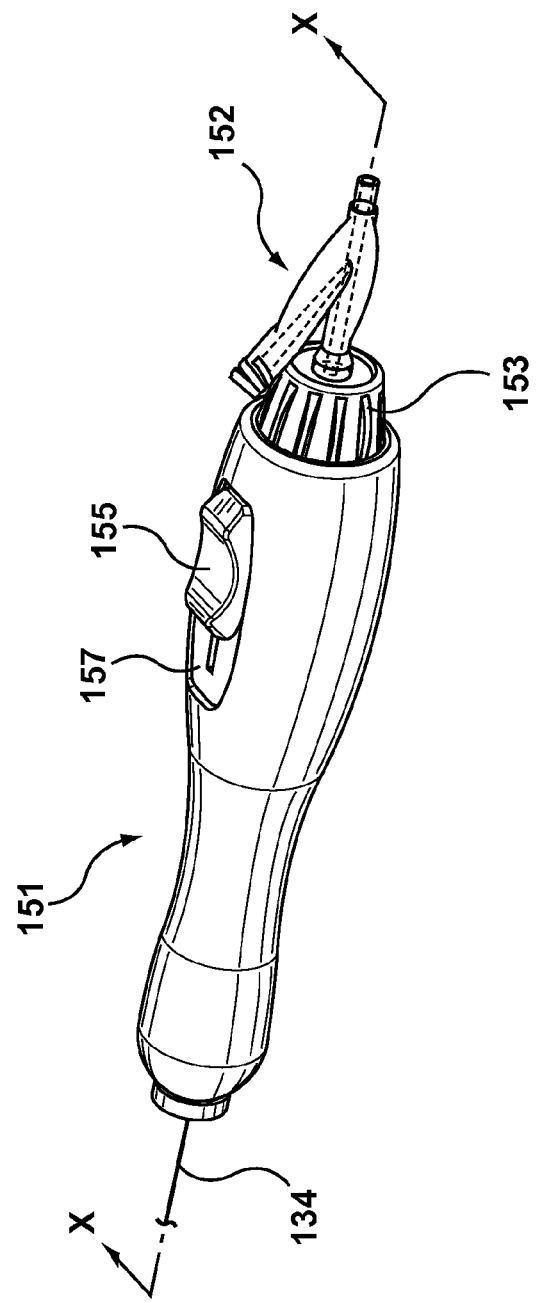
FIG. 26 is a perspective view of the handle of the occlusion bypassing apparatus of FIG. 1.

In addition to alternative cut designs, needle housings according to embodiments hereof may be formed with alternative curved distal portions. More particularly, FIG. 25 illustrates a distal portion 2520 of a needle housing 2516 according to another embodiment hereof, wherein the distal portion of the needle housing includes two continuous curved portions 2520A, 2520B along its length. Curved portion 2520B extends in a first or upward direction while curved portion 2520A extends in a second or downward direction that opposes the first direction. As will be understood by those of ordinary skill in the art, the terms upward and downward are relative terms and used for illustrative purposes only. Similar to curved distal portion 120 of needle housing 116, distal portion 2520 of needle housing 2516 is formed with the same curvature as curved distal end 136 of needle component 134 so that an automatic centering design is obtained. Essentially, curved portion 2520A is the same as curved distal portion 120 of needle housing 116 while curved portion 2520B is an extension that increases the overall length of distal portion 2520 of needle housing 2516.

Increasing the overall length of distal portion 2520 of needle housing 2516 increases the amount of material that matches or corresponds to the curved distal end of the needle component advanced there-through, thereby ensuring that the needle component is very stable inside the needle housing.

Figure 12:
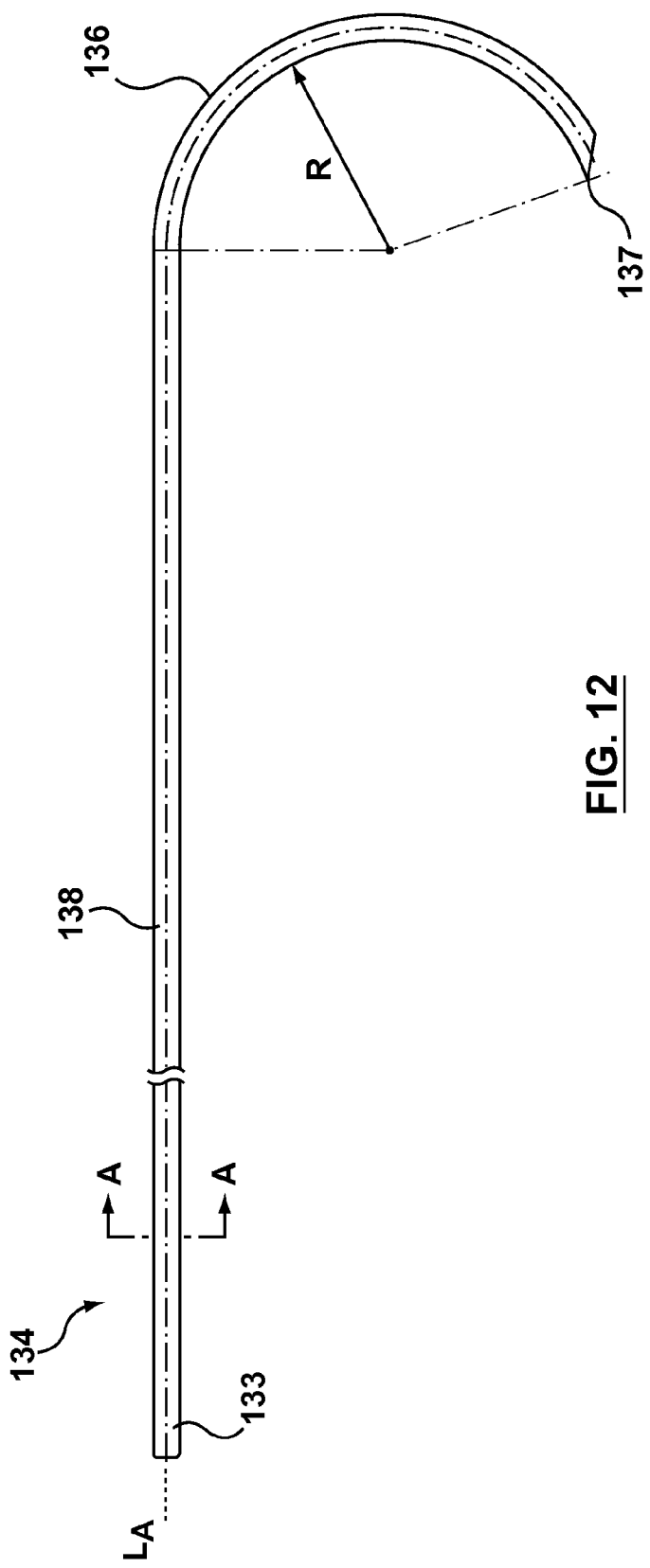
FIG. 12 is a side view of the needle component of the occlusion bypassing apparatus of FIG. 1, wherein the needle component is removed from the occlusion bypassing apparatus.
Figure 12A:
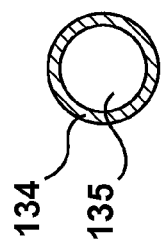
FIG. 12A is a cross-sectional view of the needle component of FIG. 12 taken along line A-A thereof.

Needle component 134, which is shown removed from occlusion bypassing apparatus 100 in FIG. 12, is a tubular or cylindrical element that is configured to be slidably disposed within lumen 112 of inner shaft component 110 and removable therefrom. More particularly, needle component 134 is disposed within inner shaft component 110 such that there is sufficient space or room there-between for needle component 134 to be movable or slidable in a longitudinal direction relative to inner shaft component 110. In order to accommodate a guidewire that may be utilized during a method of subintimally crossing an occlusion as will be discussed in more detail herein, needle component 134 may be a hypotube that defines a lumen 135 there-through as shown in the cross-sectional view of FIG. 12A. In an embodiment, lumen 135 of needle component 134 is sized to accommodate a guidewire having an outer diameter equal to or less than 0.014 inch such that occlusion bypassing apparatus 100 has a low profile. As shown in FIG. 1, a proximal end 133 of needle component 134 extends out of the patient from hub 152 to be manipulated by a clinician and a distal tip 137 of needle component 134 is configured to pierce or penetrate through a wall of a vessel when extended or deployed.

Occlusion bypassing apparatus 100 may have a handle 151 coupled thereto in order to assist in the manipulation of needle component 134 and outer shaft component 102. As shown in FIG. 1 and FIGS. 26-28, handle 151 includes a knob or cogwheel 153 and a slider 155. Knob 153 is attached to outer shaft component 102 such that rotation of the knob results in rotation of the outer shaft, as well as at least the inner shaft component. More particularly, if a user needs to rotate outer shaft component 102 in order to orient side port 108 towards a true lumen of a vessel, the user turns knob 153 to manipulate outer shaft component 102 as desired. Slider 155 is attached to needle component 134 such that operation of slider 155 results in deployment or retrieval of the needle component. More particularly, when it is desired to deploy or retrieve needle component 134, slider 155 is pushed or pulled within a recess 157 formed on handle 151. Handle 151 also includes a tubular component 2861 (shown in FIG. 28) that houses needle component 134 within the handle in order to prevent kinking of the needle component. Further, handle 151 also includes a flushing luer 2863 so that occlusion bypassing apparatus 100 may be flushed prior to use within the vasculature in accordance with techniques known in the field of interventional cardiology and/or interventional radiology. Flushing of occlusion bypassing apparatus 100 is described in more detail herein.

Needle component 134 includes an elongated first or proximal segment 138 that extends substantially parallel with longitudinal axis $L_A$ of occlusion bypassing apparatus 100 and curved distal end 136 distally extending from a distal end of proximal segment 138. Curved distal end 136 is pre-formed in a bent or curved shape or configuration. More particularly, as shown in FIG. 12, curved distal end 136 extends, bends, or otherwise curves in a circular path. In an embodiment hereof, curved distal end 136 extends in a circular path approximately 160° from a distal end of proximal segment 138, thereby forming a portion of a circle having a radius R. "Approximately" as used herein includes angles with a plus or minus 20° error margin. In an embodiment hereof, radius R is 5 mm. At least curved distal end 136 of needle component 134 is formed from a biocompatible resilient metal such as spring temper stainless steel or nitinol, which utilizes the elastic properties of stress induced martensite, such that a heat or thermal treatment of the selected material may be used to set the shape of curved distal end 136. In an embodiment, needle component 134 may be formed from more than one material, for e.g., with proximal segment 138 being formed of stainless steel and only curved distal end 136 being formed of nitinol. With additional reference to FIG. 6, curved distal portion 120 of needle housing 116 is formed with the same curvature as curved distal end 136 of needle component 134 so that an automatic centering design is obtained. More particularly, curved distal portion 120 of needle housing 116 includes a bend or turn that corresponds with, matches or is the same as the bend or turn of curved distal end 136 of needle component 134. The bend of curved distal portion 120 of needle housing 116 is formed with the same radius R as the bend of curved distal end 136 of needle component 134 so that the needle component 134 exits side port 108 of outer shaft component 102 at or with the correct orientation for re-entry of a true lumen of a vessel. By forming curved distal portion 120 of needle housing 116 and curved distal end 136 of needle component 134 with identical curvatures or radiuses, needle component 134 is very stable inside needle housing 116, thus minimizing any rotation or relative movement between the two components, especially during the needle deployment.

Figure 4:
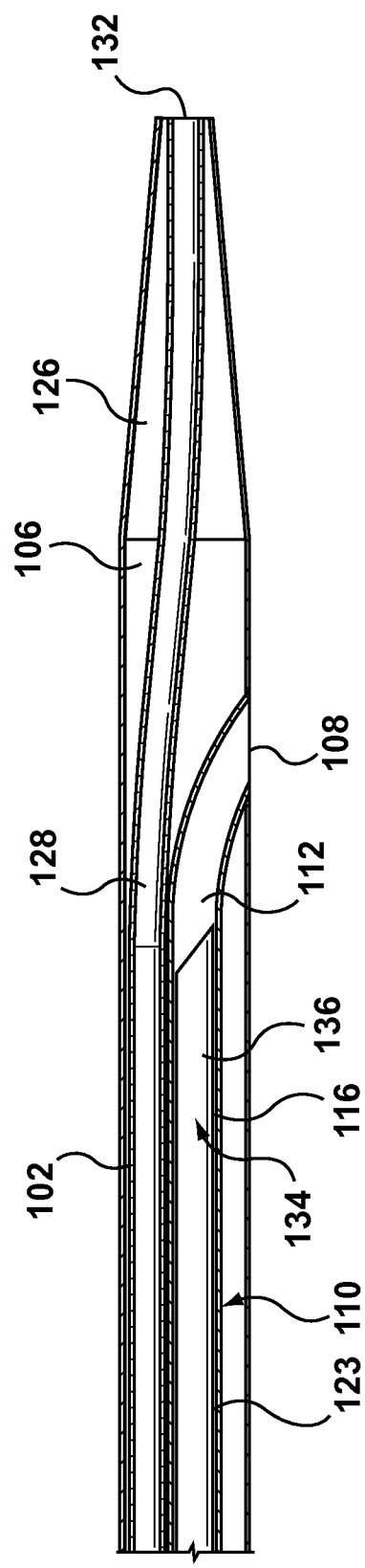
FIG. 4 is a partial longitudinal sectional view of the occlusion bypassing apparatus of FIG. 1 taken along line D-D thereof, wherein the occlusion bypassing apparatus is shown in a delivery configuration in which a needle component thereof resides within the inner shaft component of the occlusion bypassing apparatus.

With reference now to FIG. 4, in a first or delivery configuration of the apparatus the curved distal end 136 of needle component 134 is held or restrained in a straightened form within needle housing 116 of inner shaft component 110. Balloons 122A, 122B and inflation shaft 124 are not shown in FIG. 4 since the sectional view is taken approximately through the midline of occlusion bypassing apparatus 100. Needle housing 116 is formed from a relatively stiff or less flexible material as described above in order to effectively straighten curved distal end 136 of needle component 134. More particularly, in an embodiment hereof, needle component 134 is pre-loaded within inner shaft component 110 and curved distal end 136 of needle component 134 is held or restrained in a straightened form within straightening portion 123 of needle housing 116 which has no apertures or cut-out portions formed therein. Since transition portion 118 is formed with pairs of aligned apertures 142 to achieve varying flexibility, straightening portion 123 of needle housing 116 with no apertures or cut-out portions is relatively stiffer or less flexible to ensure straightening of curved distal end 136 of needle component 134. Straightening portion 123 of needle housing 116 holds the curved distal end of the needle component in a straightened form during advancement of occlusion bypassing apparatus 100 in the human vasculature.

In a second configuration of the apparatus, best shown in the sectional view of FIG. 1D, curved distal end 136 of needle component 134 extends from side port 108 of outer shaft component 102 and bends or curves from longitudinal axis $L_A$ of the apparatus. Balloons 122A, 122B and inflation shaft 124 are not shown in FIG. 1D since the sectional view is taken approximately through the midline of occlusion bypassing apparatus 100. More particularly, when it is desired to transform the apparatus from the first configuration to the second configuration, it must first be confirmed that side port 108 of outer shaft component 102 is positioned beyond or distal to the target occlusion and is oriented in the direction of the true lumen of the vessel. The position and orientation of occlusion bypassing apparatus may be monitored via the radiopaque markers of apparatus 100. Once side port 108 is positioned and oriented as desired, needle component 134 is distally advanced relative to inner shaft component 110 such that curved distal end 136 is no longer constrained by needle housing 116 of inner shaft component 110 but rather is extended to protrude from side port 108 of outer shaft component 102. When released from needle housing 116, curved distal end 136 resumes its pre-formed shape or geometry by its own internal restoring forces. As described with respect to FIG. 12, curved distal end 136 extends, bends, or otherwise curves in a circular path, thereby forming a portion of a circle having a radius R. When needle component 134 is distally advanced or extended as best shown in FIGS. 1 and 3, distal tip 137 may be used to penetrate through the vessel wall and re-enter a true lumen of a vessel as described herein. As described above, by forming the bend of curved distal end 136 of needle component 134 with the same curvature or radius as the bend of curved distal portion 120 of needle housing 116, deployed needle component 134 is very stable inside needle housing 116, thus minimizing any rotation or relative movement between the two components. Lateral balloons 122A, 122B may be expanded or inflated to anchor outer shaft component 102 within a subintimal tract either before or after the distal advancement of needle component 134. In an alternative method of the present invention, according to the physician's experience during the procedure he may realize that the subintimal space is sufficiently narrow and suitably envelops the occlusion bypassing apparatus that the latter is properly anchored within the subintimal space. Therefore, in this case there could be no need for expanding the lateral balloons.

As previously stated, in addition to radiopaque marker 160 of inner shaft component 110, occlusion bypassing apparatus 100 may include additional radiopaque markers in order to visually monitor the location of the apparatus in situ as well as the orientation of the apparatus. Each marker has an individual function or advantage, and collectively, the relative positioning of the multiple markers may be utilized to detect device orientation. As shown in FIG. 1, a first radiopaque marker 162 may be coupled to distal tip 126 of occlusion bypassing apparatus 100 and a second radiopaque marker 164 may be coupled adjacent to distal tip 137 of needle component 134. First radiopaque marker 162 provides visibility during delivery and advancement of the occlusion bypassing apparatus. Second radiopaque marker 164 improves visibility of needle component 134 and allows a user to visually check and then correctly track the deployment of the needle component. Radiopaque marker 160, which may be considered a third radiopaque marker, allows a user to properly position occlusion bypassing apparatus 100 across an occlusion or lesion in situ and unequivocally identify the position of the side port 108. Collectively, the relative positioning of the radiopaque markers allow a user to identify or track the apparatus rotation across the lesion and proper needle orientation during deployment thereof. Markers 160, 162, 164 may be formed with different shapes, different dimensions, and/or different materials having different levels of radiopacity so that they may be distinguished from each other when in situ. For example, in an embodiment hereof, first marker 162 is formed from Pt—Ir, second marker 164 is formed from gold, and third marker 160 is formed from tantalum.

Figure 29:
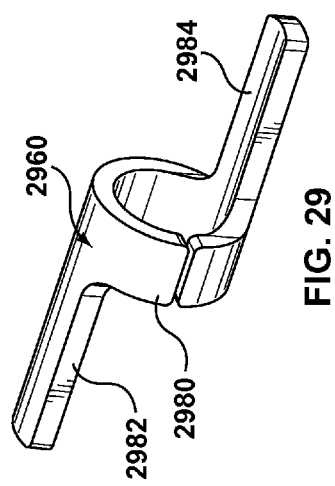
FIG. 29 is a perspective view of a radiopaque marker that may be utilized in embodiments hereof, wherein the radiopaque marker has an S-shape.
Figure 30:
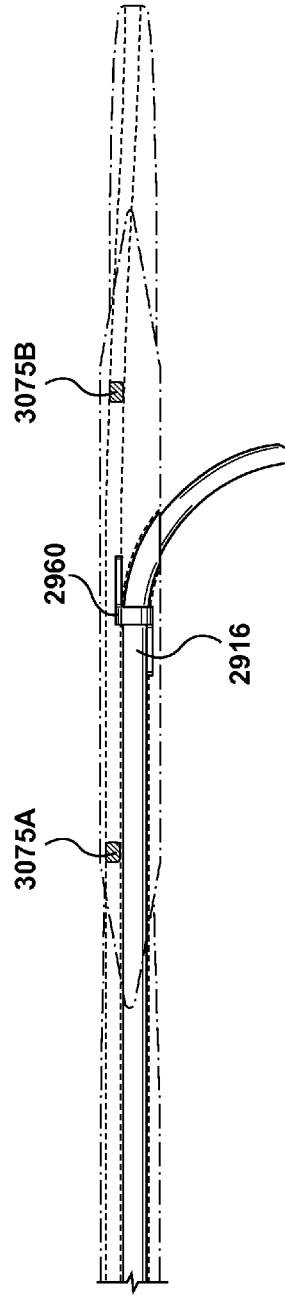
FIG. 30 is a side view of a distal portion of the occlusion bypassing apparatus of FIG. 1, wherein the occlusion bypassing apparatus includes the radiopaque marker of FIG. 29.
Figure 31:
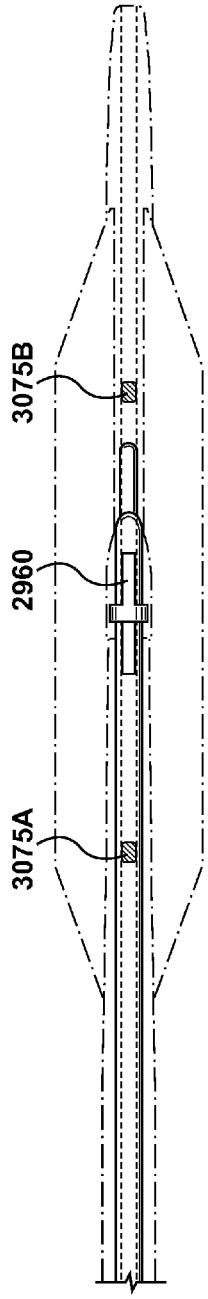
FIG. 31 is a top view of a distal portion of the occlusion bypassing apparatus of FIG. 1, wherein the occlusion bypassing apparatus includes the radiopaque marker of FIG. 29.

It will be understood by those of ordinary skill in the art that occlusion bypassing apparatuses described herein may utilize alternative radiopaque marker configurations and patterns in order to properly position the occlusion bypassing apparatus. For example, FIG. 29 illustrates an asymmetrical, S-shaped radiopaque marker 2960 that may be coupled to a distal portion of a needle housing 2916, as shown in FIG. 30 and FIG. 31 (balloons and outer shaft components are shown in phantom in FIGS. 30-31 so that the components internal thereto are clearly shown). Marker 2960 includes an annular or ring portion 2980, a first leg portion 2982, and a second leg portion 2984. Leg portions 2982, 2984 extend from opposing sides of ring portion 2980 and are 180 degrees offset from each other. As shown in the side and top views of FIG. 30 and FIG. 31, respectively, marker 2960 has a unique and distinctive shape depending upon the orientation of the occlusion bypassing apparatus. Due to the unique and asymmetrical shape of marker 2960, marker 2960 allows a user to properly position the occlusion bypassing apparatus across an occlusion or lesion in situ and unequivocally identify the position and orientation of the side port. Further as shown in the side and top views of FIG. 30 and FIG. 31, respectively, cylindrical or ring radiopaque markers 3075A, 3075B may also be included to assist in properly positioning the occlusion bypassing apparatus. Markers 3075A, 3075B may be coupled to an annular lumen of the occlusion bypassing apparatus, such as the guidewire lumen. Markers 3075A, 3075B indicate or mark the proximal and distal ends of the balloons in order to provide the user with information about balloon position. In addition, marker 3075B functions to mark the maximum axial extension of the needle component when deployed. More particularly, marker 3075B provides the user with information about the vessel portion that is potentially subject to contact the needle component when deployed.

Figure 32:
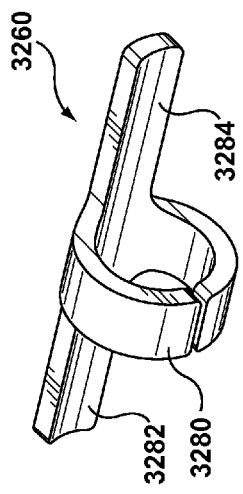
FIG. 32 is a perspective view of a radiopaque marker that may be utilized in embodiments hereof, wherein the radiopaque marker has a T-shape.
Figure 33:
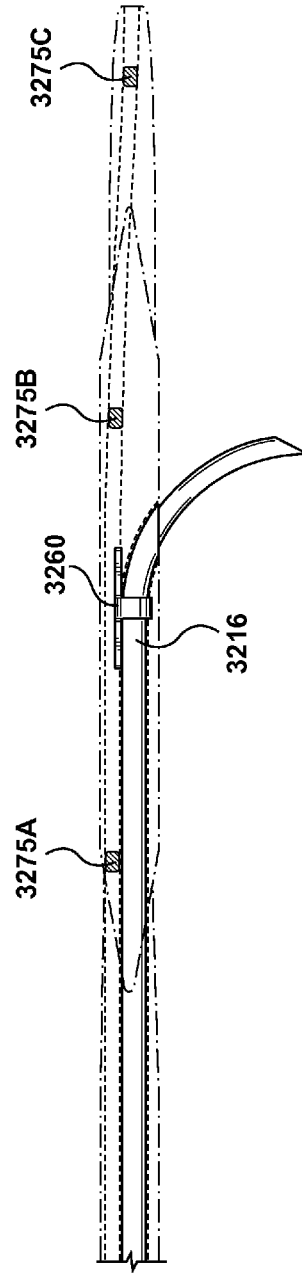
FIG. 33 is a side view of a distal portion of the occlusion bypassing apparatus of FIG. 1, wherein the occlusion bypassing apparatus includes the radiopaque marker of FIG. 32.
Figure 34:
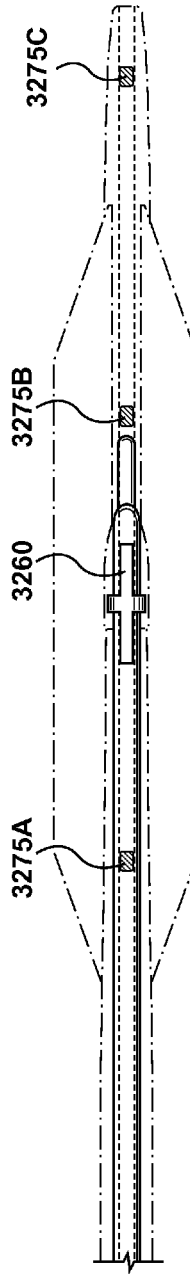
FIG. 34 is a top view of a distal portion of the occlusion bypassing apparatus of FIG. 1, wherein the occlusion bypassing apparatus includes the radiopaque marker of FIG. 32.
Figure 35:
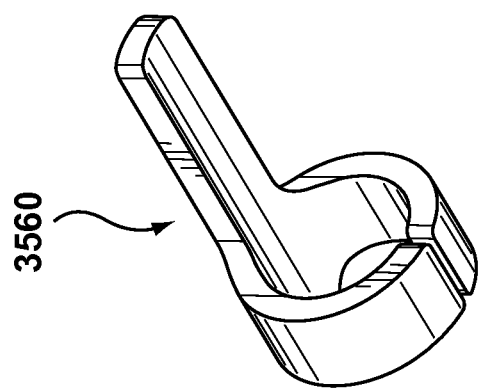
FIG. 35 is a perspective view of a radiopaque marker that may be utilized in embodiments hereof, wherein the radiopaque marker has an L-shape.

FIG. 32 illustrates another configuration of a radiopaque marker 3260 that may be used in embodiments herein. Marker 3260 may be coupled to a distal portion of a needle housing 3216, as shown in FIG. 33 and FIG. 34 (balloons and outer shaft components are shown in phantom in FIGS. 33-34 so that the components internal thereto are clearly shown). Marker 3260 is generally T-shaped and includes an annular or ring portion 3280, a first leg portion 3282, and a second leg portion 3284. Leg portions 3282, 3284 extend from opposing sides of ring portion 2980 but are not circumferentially offset from each other. As shown in the side and top views of FIG. 33 and FIG. 34, respectively, marker 3260 has a unique and distinctive shape depending upon the orientation of the occlusion bypassing apparatus. Due to the unique shape of marker 3260, marker 3260 allows a user to properly position the occlusion bypassing apparatus across an occlusion or lesion in situ and unequivocally identify the position and orientation of the side port. Further as shown in the side and top views of FIG. 33 and FIG. 34, respectively, cylindrical or ring radiopaque markers 3275A, 3275B, 3275C may also be included to assist in properly positioning the occlusion bypassing apparatus. Markers 3275A, 3275B, 3275C may be coupled to an annular lumen of the occlusion bypassing apparatus, such as the guidewire lumen. Markers 3275C, 3275B function similar to markers 3075A, 3075B described above. Marker 3275C marks or indicates a distal end of the apparatus. Additional marker configurations may also be used in embodiments described herein, including but not limited to an L-shaped radiopaque marker 3560 shown in FIG. 35.

Other types of construction are suitable for outer shaft component 102. In another embodiment hereof, FIG. 13 is a cross-sectional view of an alternate construction (taken along line A-A of FIG. 1) including an outer shaft component 1302 in which the lumens thereof are all formed by multi-lumen profile extrusion. More particularly, outer shaft component 1302 includes a lumen 1309 for housing inner shaft component 110 (which defines lumen 112 for housing a needle component 134 as described above), a guidewire lumen 1329 for housing a guidewire 1340, and an inflation lumen 1325. Inner shaft component 110 is positioned within or through lumen 1309 of outer shaft component 1302 and may be adhered, melted, or otherwise coupled to the inner wall of the outer shaft component. Since guidewire lumen 1329 and inflation lumen 1325 are defined by outer shaft component, internal shaft or tube components (i.e., guidewire shaft 128 and inflation shaft 124 in FIG. 1A) are not required for forming these lumens. Similar to guidewire lumen 129, guidewire lumen 1329 is relatively short and extends only through a distal portion of outer shaft component 1302 for accommodating guidewire 1340 in a so-called rapid-exchange configuration. In another embodiment shown in FIG. 14, which is a cross-sectional view taken along line A-A of FIG. 1, outer shaft component 102 includes a first inflation tube 1424A defining a first inflation lumen 1425A and a second inflation tube 1424B defining a second inflation lumen 1425B. Rather than a single inflation lumen that concurrently delivers inflation fluid to both first and second lateral balloons 122A, 122B as in the embodiment of FIG. 1A, inflation lumens 1425A, 1425B separately deliver inflation fluid to the first and second lateral balloons. In another embodiment, FIG. 15 is a cross-sectional view of an alternate construction (taken along line A-A of FIG. 1) in which inflation tube 124 and guidewire tube 128 are bonded to an outer surface of inner shaft component 110. More particularly, inflation shaft 124 defining inflation lumen 125 and guidewire shaft 128 defining guidewire lumen 129 for accommodating guidewire 140 are both bonded to an outer surface of inner shaft component 110, whereby the bonding material essentially forms an outer shaft component 1502.

Further, although embodiments above are described with a relatively short guidewire shaft in a rapid-exchange configuration, embodiments hereof may be modified to have an over-the-wire configuration in which the guidewire lumen extends the entire length of the outer shaft component. For example, in order to provide an over-the-wire configuration, the relatively short guidewire shafts of the above embodiments may be modified to extend the entire length of the outer shaft component.

Figure 36:
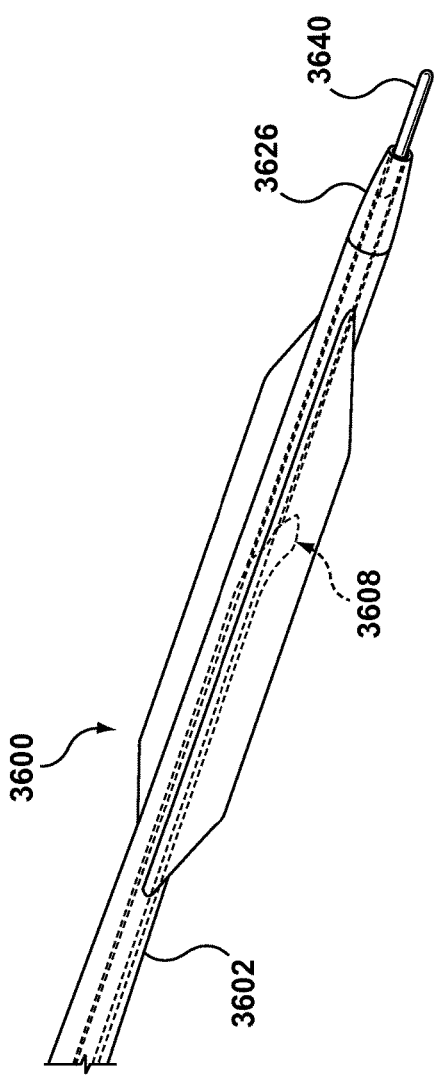
FIG. 36 is a perspective view of a distal portion of an occlusion bypassing apparatus having an over-the-wire configuration, wherein a guidewire is shown extending through an inner shaft component of the occlusion bypassing apparatus.
Figure 37:
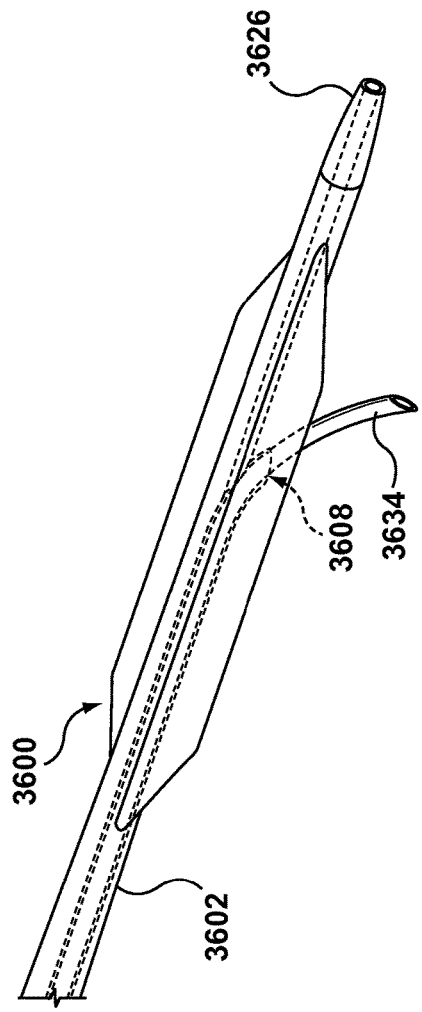
FIG. 37 is a perspective view of the occlusion bypassing apparatus of FIG. 36, wherein a needle component is shown extending through the inner shaft component of the occlusion bypassing apparatus.
Figure 38:
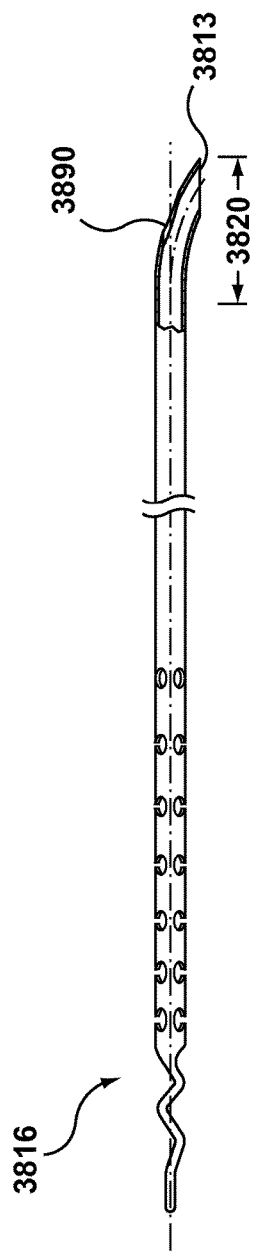
FIG. 38 is a side view of a needle housing configured for use in the occlusion bypassing apparatus of FIG. 36, wherein the needle housing is removed from the inner shaft component for illustrative purposes only.
Figure 39:
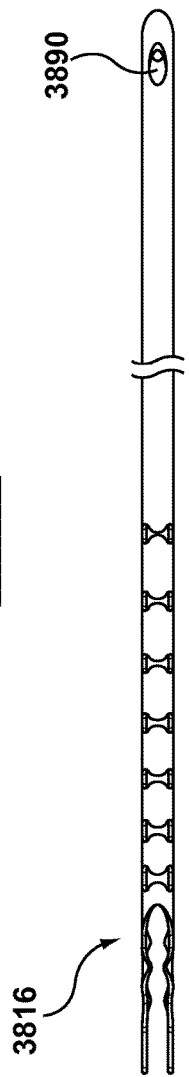
FIG. 39 is a top view of the needle housing of FIG. 38.
Figure 40:
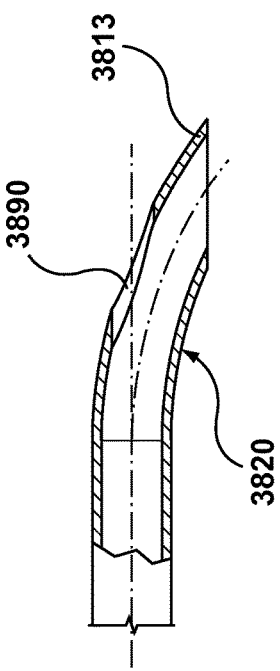
FIG. 40 is an enlarged view of a distal end of the needle housing of FIG. 38.

As another example, the relatively short guidewire shafts of the above embodiments may be removed or eliminated and the continuous lumen of the inner shaft component according to embodiments hereof may be utilized to selectively house a guidewire or a needle component. Such an over-the-wire configuration is illustrated in FIGS. 36-40. More particularly, an occlusion bypassing apparatus 3600 has an over-the-wire configuration. Similar to embodiments described above, occlusion bypassing apparatus 3600 includes an outer shaft component 3602 and an inner shaft component (not shown) extending therein, the inner shaft component including a body portion (not shown) and a needle housing 3816 that collectively form a continuous lumen there-through. Needle housing 3816 of occlusion bypassing apparatus 3600 is shown removed from the apparatus in FIGS. 38-39. Needle housing 3816 includes a distal guidewire port or opening 3890 formed on distal curved portion 3820 of the needle housing, proximal to a distal end 3813 of the needle housing which forms a side port 3608 of occlusion bypassing apparatus 3600. Distal guidewire port 3890 is sized to permit passage of a guidewire there-through but not permit passage of a needle component. As such, when a guidewire 3640 is positioned through the continuous lumen of the inner shaft component, guidewire 3640 passes through distal guidewire port 3890 and exits from a distal tip 3626 coupled to a distal end of outer shaft component 3626 as shown in FIG. 36. Guidewire 3640 is utilized when advancing occlusion bypassing apparatus 3600 over the guidewire to a target location in situ. When re-entry into a true lumen should occur, guidewire 3640 is retracted and a needle component 3634 may be distally advanced through the continuous lumen of the inner shaft component and deployed through side port 3608 as shown in FIG. 37.

Figure 16:
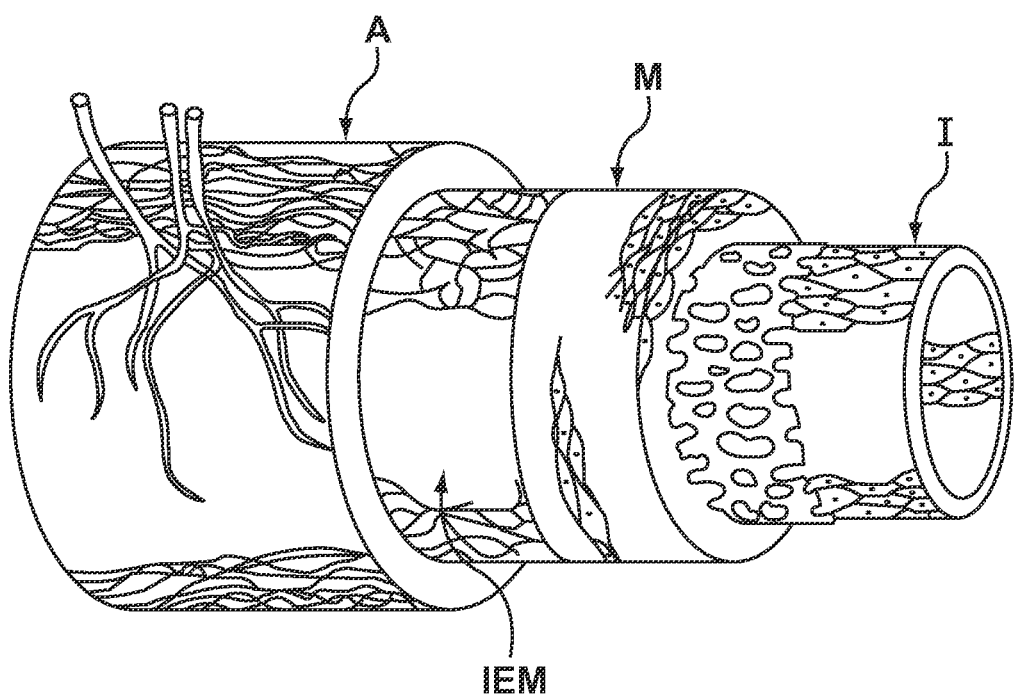
FIG. 16 is a diagram of an artery showing the three layers of tissue that comprise the artery wall.

FIG. 16 is a sectional view of the anatomy of an artery wall, which for purposes of this description is shown to consist essentially of three layers, the tunica intima I ("intima"), tunica media M ("media") which is the thickest layer of the wall, and the tunica adventitia A ("adventitia"). In some arteries an internal elastic membrane IEM is disposed between the media M and adventitia A. The adventitia A is made of collagen, vasa vasorum and nerve cells, the media M is made of smooth muscle cells, and the intima I is made up of a single layer of endothelial cells that provide a nonthrombogenic surface for flowing blood. Occlusion bypassing apparatus 100 is used as part of a system for creating a subintimal reentry tract within a wall of a blood vessel V to allow blood flow around an occlusion. FIGS. 17-24 illustrate an exemplary method of using the above-described occlusion bypassing apparatus 100 to bypass a chronic total occlusion (CTO) according to an embodiment hereof. Although described in relation to bypassing a CTO, it should be understood that the methods and apparatus described herein may be used for bypassing any tight stenoses in arteries or other anatomical conduits and are not limited to total occlusions.

Prior to use of occlusion bypassing apparatus 100 within the vasculature, it may be desirable to flush the apparatus in accordance with techniques known in the field of interventional cardiology and/or interventional radiology. Flushing of occlusion bypassing apparatus 100 may be performed through lumen 135 of needle component 134. More particularly, small openings or holes (not shown) may be provided on needle component 134. In order to perform the initial flushing of occlusion bypassing apparatus 100, side port 108 of outer shaft component 102 is occluded. Saline solution is introduced into a proximal end of lumen 135 of needle component 134 and flushes lumen 135. Since side port 108 is occluded, the saline solution exits from the small holes formed on needle component 134 and flushes lumen 112 of inner shaft component.

Figure 17:
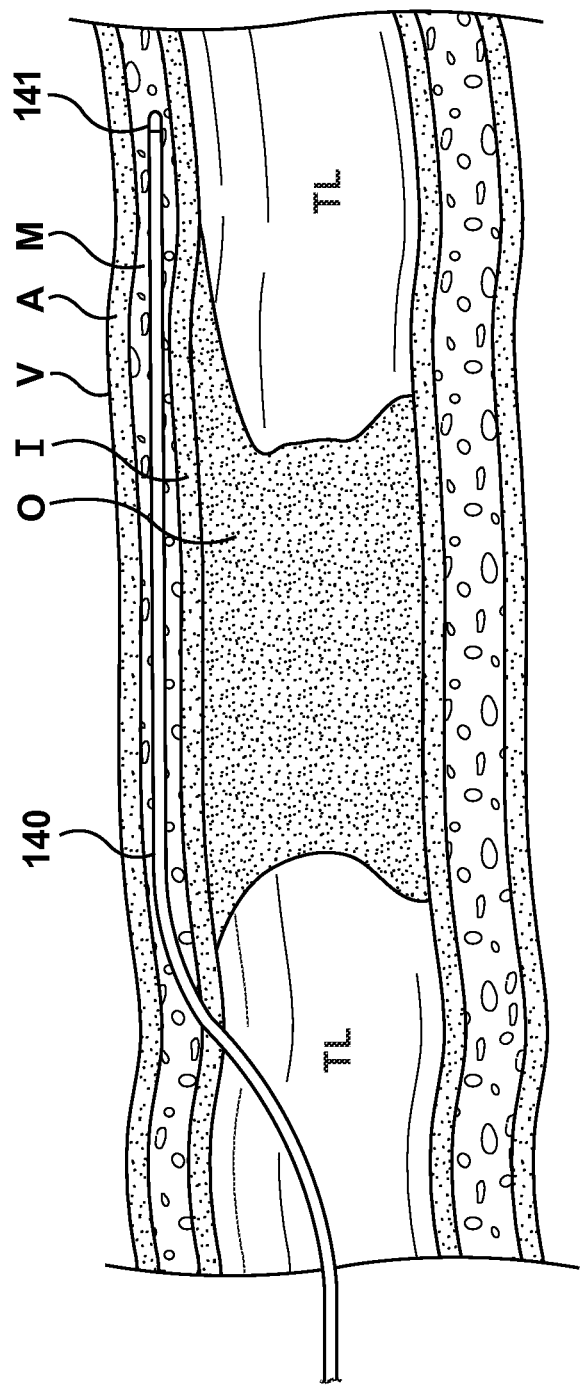
FIG. 17 illustrates a step of a method of crossing an occlusion within a vessel, wherein a guidewire has been transluminally advanced through the vasculature to a position upstream of a treatment site, which in this instance is shown as occlusion O within a true lumen TL of blood vessel V.

As shown in FIG. 17, in accordance with techniques known in the field of interventional cardiology and/or interventional radiology, guidewire 140 having a distal end 141 is transluminally advanced through the vasculature to a position upstream of a treatment site, which in this instance is shown as occlusion O within a true lumen TL of blood vessel V. Guidewire 140 pierces the intima I and is advanced distally to create a subintimal tract by locally dissecting or delaminating intima I from media M or by burrowing through media M. In order to pierce the intima I, a clinician may manipulate distal end 141 of guidewire 140 by prolapsing or bending-over the distal end of guidewire 140 (not shown) and thereafter may use the stiffer arc or loop of the prolapsed distal end to pierce into the intima I to advance guidewire 140 there through. The piercing of the intima I is aided by the fact that typically blood vessel V is diseased, which in some instances makes the intima I prone to piercing. Guidewire 140 is distally advanced within the subintimal tract from a near side of occlusion O to a position where distal end 141 thereof is positioned in the subintimal tract on a far side of occlusion O.

Alternatively, another device other than guidewire 140 initially may be used to create the subintimal tract. Those of ordinary skill in the art will appreciate and understand the types of alternative devices that may be used in this step including an apparatus known as an "olive", a laser wire, an elongate radiofrequency electrode, a microcatheter, or any other device suitable for boring or advancing through the vessel tissue. As another example, a guidewire other than guidewire 140 may be utilized to create the subintimal tract. More particularly, a guidewire having a relatively larger outer diameter than guidewire 140, such as between 0.032-0.040 inches, may be utilized to create the subintimal tract because a larger guidewire has greater column strength to gain access to the subintimal space of vessel V. If an alternative device is used instead of guidewire 140 to form the subintimal tract, such alternative device may be removed and replaced with guidewire 140 after the subintimal tract has been formed.

Figure 18:
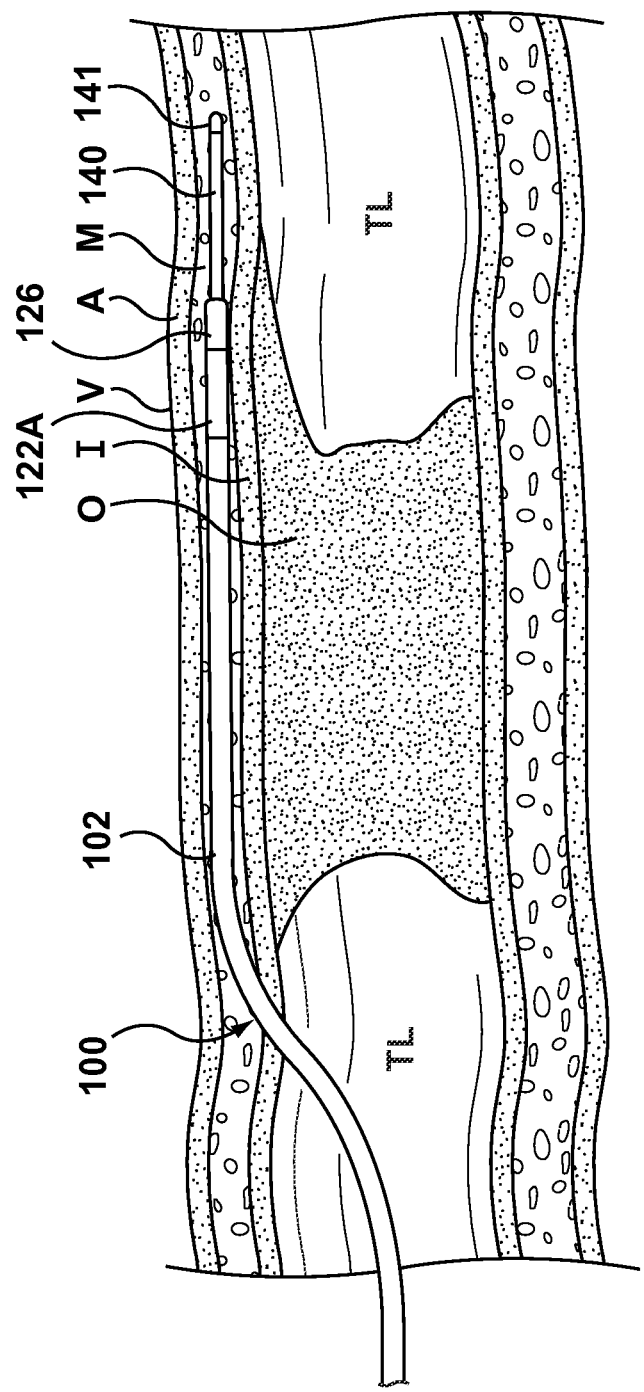
FIG. 18 illustrates another step of a method of crossing an occlusion within a vessel, wherein the occlusion bypassing apparatus of FIG. 1 is tracked over the guidewire.

After the subintimal tract is formed and guidewire 140 is in place as desired, occlusion bypassing apparatus 100 may be tracked over guidewire 140 and advanced such that distal tip 126 is adjacent to the far or downstream end of occlusion O as shown in FIG. 18. In an embodiment, needle component 134 is pre-loaded within inner shaft component 110. During the step of advancing occlusion bypassing apparatus 100 over guidewire 140, curved distal end 136 of needle component 134 is held or restrained in a straightened form within needle housing 116 as described above. Utilizing the radiopaque markers of apparatus 100, occlusion bypassing apparatus 100 should be positioned and oriented such that side port 108 of outer shaft component 102 is positioned beyond or distal to the target occlusion and is oriented in the direction of the true lumen of the vessel.

Figure 19:
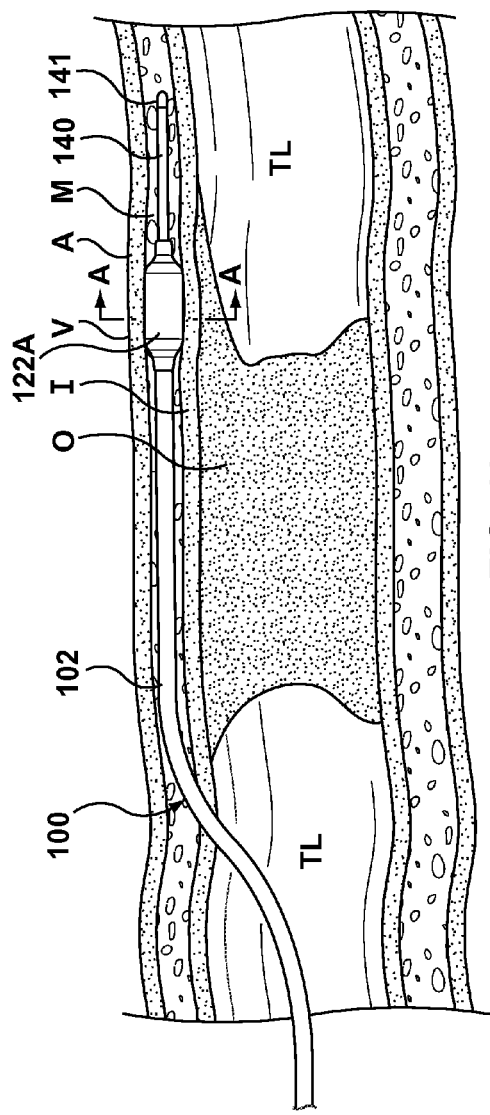
FIG. 19 illustrates another step of a method of crossing an occlusion within a vessel, wherein balloons of the occlusion bypassing apparatus are inflated to anchor the apparatus within the subintimal space.
Figure 19A:
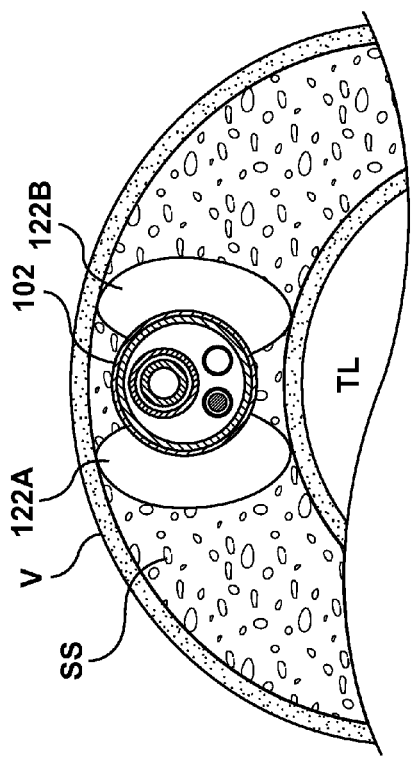
FIG. 19A is a cross-sectional view of a portion of the vessel of FIG. 19, taken along line A-A of FIG. 19.

Once outer shaft component 102 is positioned as desired, lateral balloons 122A, 122B may be expanded or inflated as shown in FIG. 19 and FIG. 19A, thus anchoring outer shaft component 102 in the subintimal tract. FIG. 19A illustrates a cross-sectional view of apparatus 100 within a vessel V having a true lumen TL and a subintimal space SS. The subintimal space SS may be described as having an arc, curve, or C shape. When inflated, lateral balloons 122A, 122B expand into contact with the surrounding patient's anatomy to fill out or occupy the subintimal space SS to improve anchoring and to minimize damage to the surrounding anatomy. In addition, although lateral balloons 122A, 122B are described herein for providing stabilization during distal advancement or deployment of needle component 134, in another embodiment hereof (not shown) inflation of lateral balloons 122A, 122B may also be used to create or assist in creating the subintimal tract. In such an embodiment, lateral balloons 122A, 122B may be inflated multiple times in the subintima to initially support delivery of the occlusion bypassing apparatus across the lesion within the subintima and then subsequently during a re-entry procedure.

Figure 20:
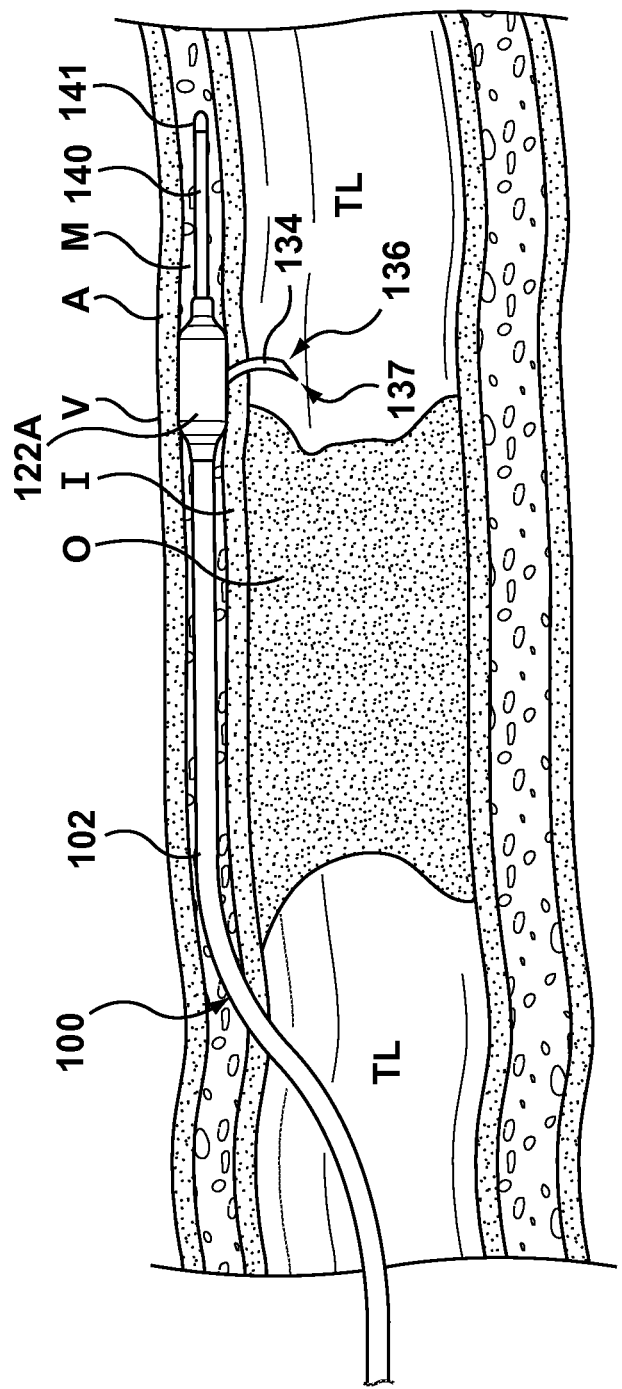
FIG. 20 illustrates another step of a method of crossing an occlusion within a vessel, wherein a needle component of the occlusion bypassing apparatus is distally advanced and deployed out of a side port of the outer shaft component.

With reference to FIG. 20, needle component 134 is distally advanced relative to inner shaft component 110 until curved distal end 136 extends from or protrudes out of side port 108 of outer shaft component 102 such that distal tip 137 of the needle component penetrates the intima to gain access to the true lumen of the vessel distal to, i.e., downstream of, the CTO. More particularly, needle component 134 is distally advanced relative to inner shaft component 110 such that curved distal end 136 is no longer constrained by needle housing 116 of inner shaft component 110 but rather is extended to protrude from side port 108 of outer shaft component 102. When released from needle housing 116, curved distal end 136 resumes its pre-formed shape or geometry by its own internal restoring forces. As described with respect to FIG. 12, curved distal end 136 extends, bends, or otherwise curves in a circular path, thereby forming a portion of a circle having a radius R. When needle component 134 is distally advanced or extended as in FIG. 20, distal tip 137 may be used to penetrate through the vessel wall and re-enter a true lumen of a vessel. As described above, by forming the bend of curved distal end 136 of needle component 134 with the same curvature or radius as the bend of curved distal portion 120 of needle housing 116, deployed needle component 134 is very stable inside needle housing 116, thus minimizing any rotation or relative movement between the two components.

Figure 21:
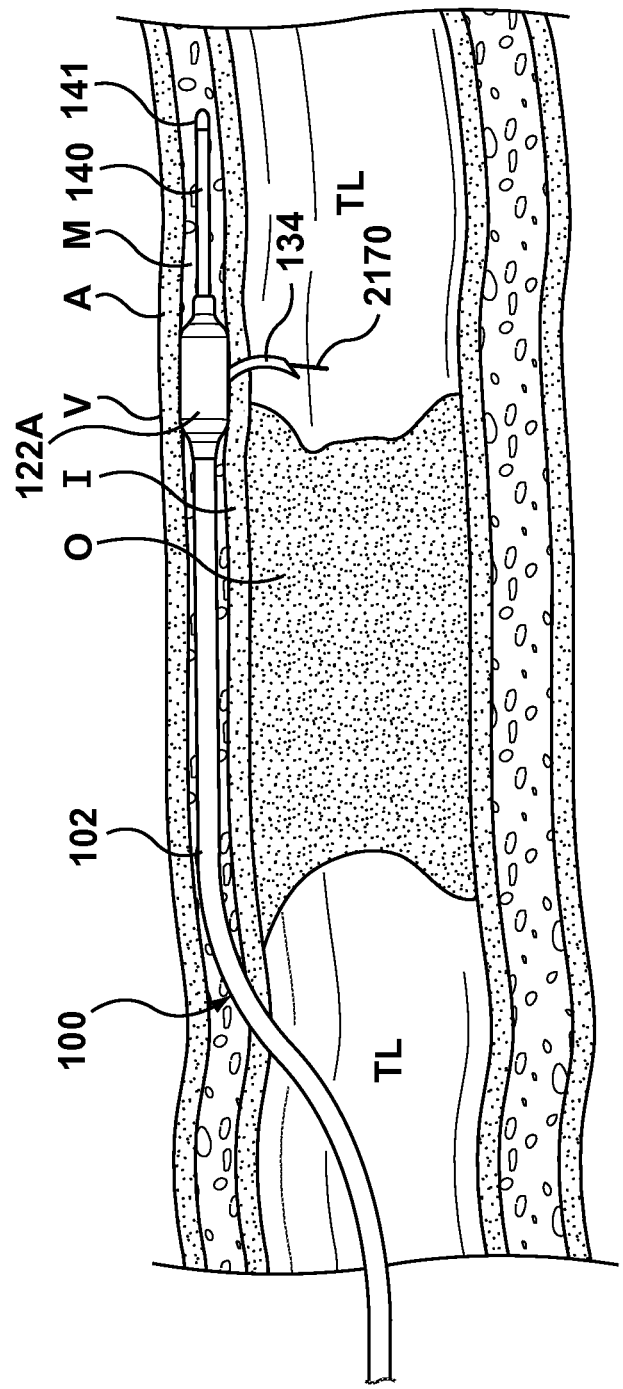
FIG. 21 illustrates another step of a method of crossing an occlusion within a vessel, wherein a second guidewire is advanced through the deployed needle component.
Figure 22:
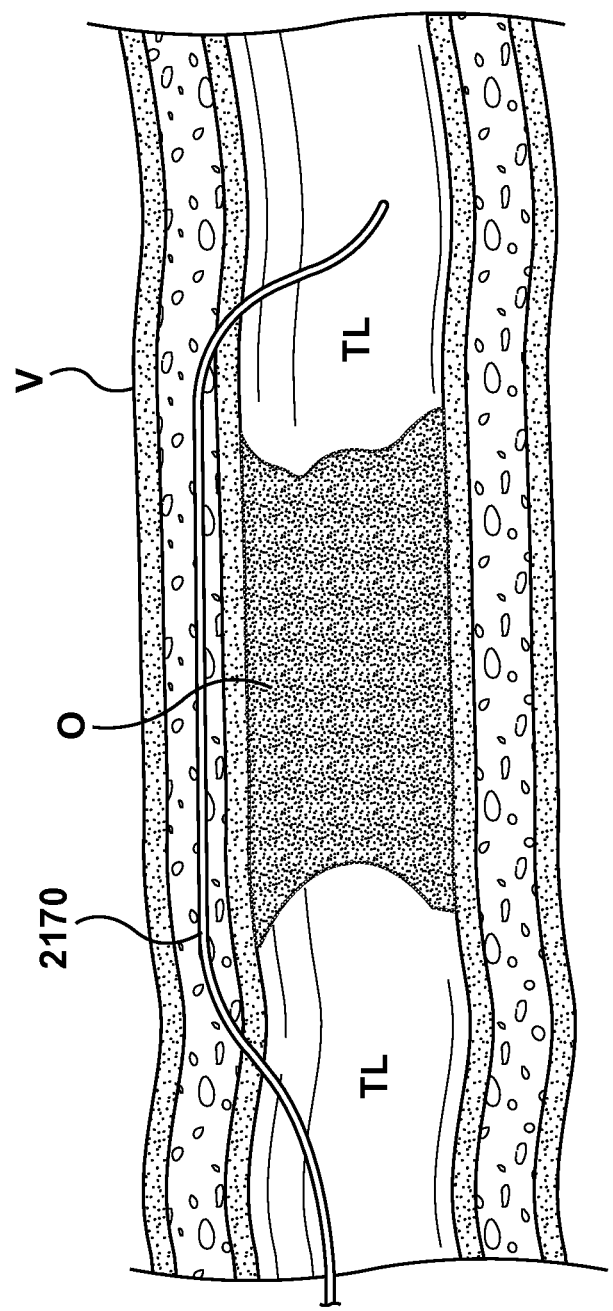
FIG. 22 illustrates another step of a method of crossing an occlusion within a vessel, wherein the occlusion bypassing apparatus is retracted and removed, leaving only the second guidewire in place.

A second guidewire 2170 may be advanced through lumen 135 of needle component 134 and into the true lumen TL of vessel V as shown in FIG. 21. Guidewire 2170 has a relatively smaller outer diameter such as 0.014 inches in order to minimize the size of needle component 134 and subsequently, minimize the size of occlusion bypassing apparatus 100. Additionally, occlusion bypassing apparatus 100 may be removed and guidewire 2170 may be left in place as shown in FIG. 22, with guidewire 2170 extending in true lumen TL proximal to the CTO, through the subintimal tract, and back into true lumen TL distal to the CTO such that the CTO may now be successfully crossed via the pathway or conduit thus created.

Figure 23:
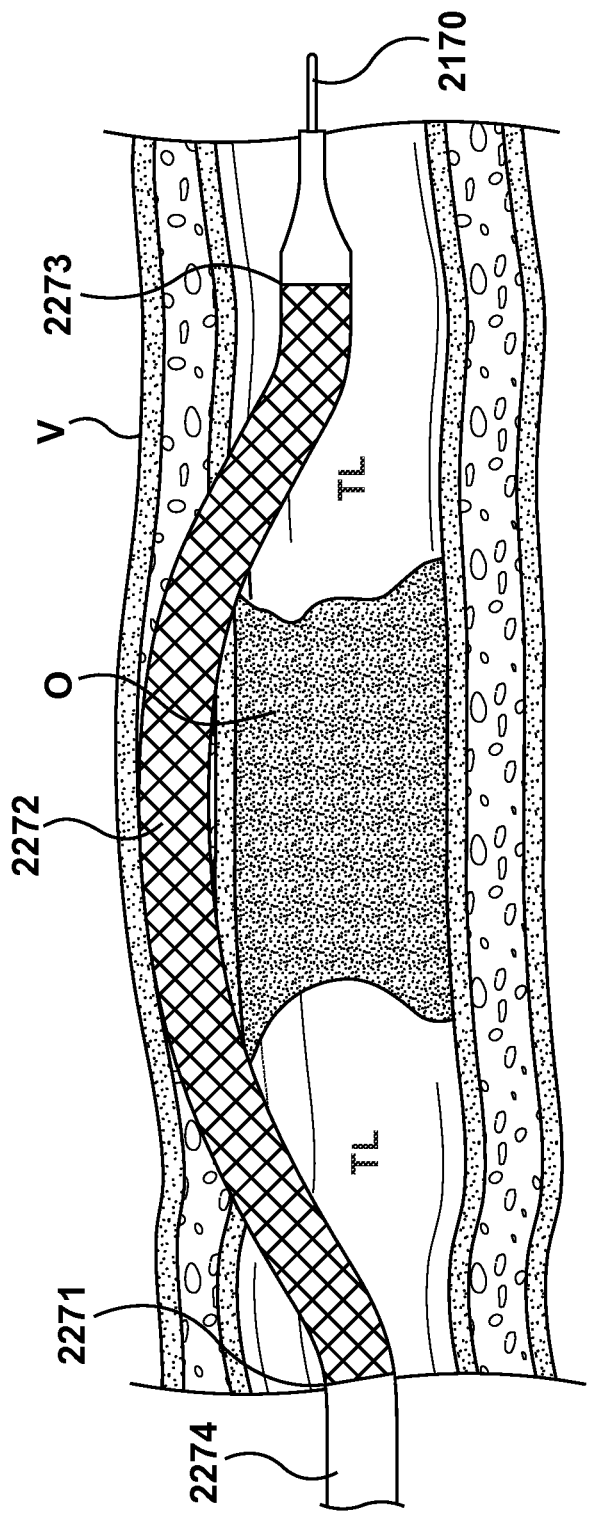
FIG. 23 illustrates another step of a method of crossing an occlusion within a vessel, wherein a stent delivery catheter is tracked over the second guidewire and the stent is expanded.
Figure 24:
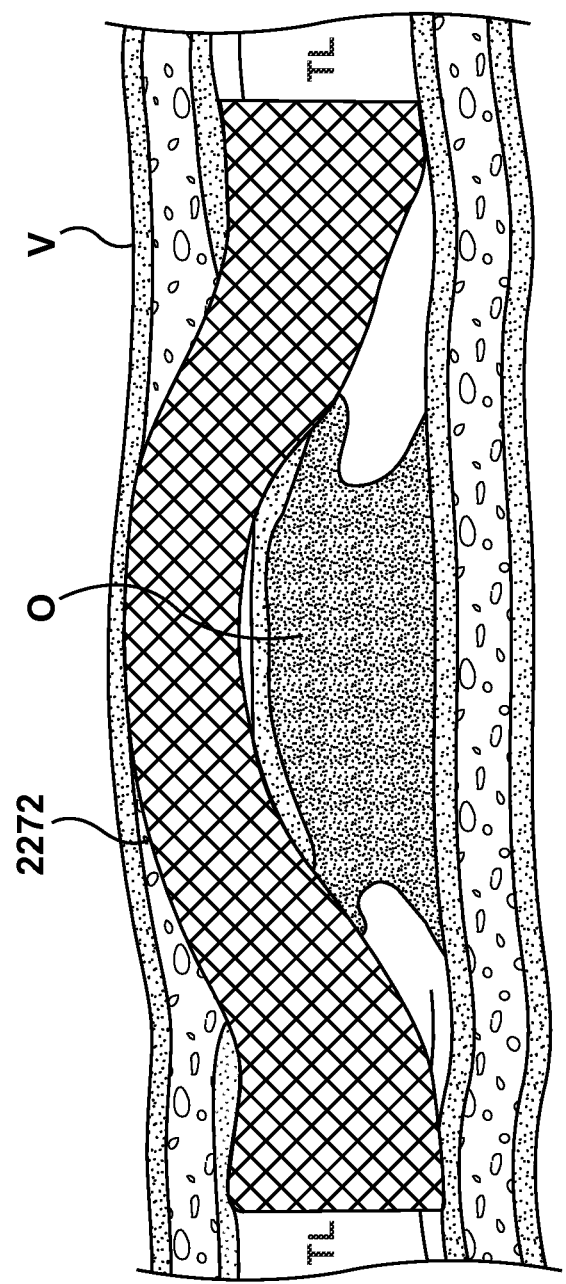
FIG. 24 illustrates another step of a method of crossing an occlusion within a vessel, wherein the stent delivery catheter and second guidewire are retracted and removed, leaving only the expanded stent in place.

Additionally, a covered or uncovered stent may be delivered over guidewire 2170 and implanted within the subintimal tract to facilitate flow from the lumen of the vessel upstream of the CTO, through the subintimal tract and back into the lumen of the vessel downstream of the CTO. FIG. 23 shows a distal end of a catheter 2274 having a stent 2272 mounted thereon being advanced over guidewire 2170 to a position where a distal end 2273 of the radially collapsed stent 2272 is in true lumen TL of vessel V downstream of chronic total occlusion CTO, a proximal end 2271 of stent 2272 is in true lumen TL of vessel V upstream of chronic total occlusion CTO, and a tubular body of stent 2272 extends through the subintimal tract. Stent 2272 is then deployed by either self-expansion or balloon inflation within the subintimal reentry tract to dilate the subintimal tract and compress the adjacent chronic total occlusion CTO. Stent 2272 provides a scaffold which maintains the subintimal tract in an open condition capable of carrying blood downstream of chronic total occlusion CTO. Thereafter, guidewire 2170 and catheter 2274 may be removed from the patient, leaving stent 2272 in an expanded configuration and creating a radially supported, subintimal blood flow channel around chronic total occlusion CTO as seen in FIG. 24. In some cases, it may be desirable to enlarge the diameter of the subintimal tract before advancing stent catheter 2274 into and through it. Such enlargement of the subintimal tract may be accomplished by passing a balloon catheter over guidewire 2170 and inflating the balloon to dilate the tract, or may be any other suitable tract enlarging, dilating or de-bulking instrument that may be passed over guidewire 2170.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. An apparatus for bypassing an occlusion in a blood vessel comprising:
   an outer shaft component having a side port proximal to a distal end thereof;
   an inner shaft component disposed within the outer shaft component and defining a continuous lumen therethrough, the inner shaft component having
      a body portion that extends substantially parallel with a longitudinal axis of the apparatus, and
      a needle housing distally extending from a distal end of the body portion, the needle housing including a curved distal portion that bends from the longitudinal axis of the apparatus and terminates at the side port of the outer shaft component and a transition portion positioned between the body portion of the inner shaft component and the curved distal portion of the needle housing,
   wherein the transition portion has a variable flexibility along a length thereof that decreases in a distal direction, the transition portion including a plurality of apertures configured to provide the transition portion with the variable flexibility and the plurality of apertures including pairs of apertures that align with each other along a transverse axis of the needle housing, each aperture in each pair of aligned apertures having an hourglass shape; and
   a needle component configured to be slidably disposed within the continuous lumen of the inner shaft component and removable therefrom, the needle component having a curved distal end with the same curvature as the curved distal portion of the needle housing.

2. The apparatus of claim 1, wherein the outer shaft component includes at least one balloon disposed proximal to the distal end thereof and an inflation lumen in fluid communication with the at least one balloon.

3. The apparatus of claim 2, wherein the side port of the outer shaft component is disposed midway along the length of the at least one balloon.

4. The apparatus of claim 2, wherein the at least one balloon includes a first lateral balloon and a second lateral balloon disposed in parallel on opposing sides of the outer shaft component.

5. The apparatus of claim 1, wherein the body portion of the inner shaft component includes a polymeric tube and the needle housing is formed from a tube of a shape memory material.

6. The apparatus of claim 5, wherein a proximal end of the needle housing includes two opposing tabs attached to the distal end of the body portion of the inner shaft component.

7. The apparatus of claim 5, wherein a portion of the tube formed from the shape memory material is replaced with a radiopaque marker having the same inner diameter and the same outer diameter as the tube formed from-the shape memory material.

8. The apparatus of claim 1, wherein spacing between adjacent apertures increases in a distal direction.

9. The apparatus of claim 1, wherein widths of adjacent apertures decrease in a distal direction.

10. The apparatus of claim 1, wherein the transition portion allows for bending of the inner shaft component only along a vertical plane passing through the longitudinal axis of the apparatus but not in other directions.

11. The apparatus of claim 1, wherein the outer shaft component includes a guidewire lumen extending at least along a distal portion thereof.

12. An apparatus for bypassing an occlusion in a blood vessel comprising:
   an outer shaft component having a side port proximal to a distal end thereof;
   an inner shaft component disposed within the outer shaft component and defining a continuous lumen therethrough, the inner shaft component having a body portion that extends substantially parallel with a longitudinal axis of the apparatus and a needle housing distally extending from a distal end of the body portion, the needle housing including a curved distal portion that bends from the longitudinal axis of the apparatus and terminates at the side port of the outer shaft component and a transition portion positioned between the body portion of the inner shaft component and the curved distal portion of the needle housing, wherein the apparatus is more flexible along the body portion of the inner shaft component than along the curved distal portion of the needle housing and the transition portion has a variable flexibility along a length thereof that decreases in a distal direction; and
   a needle component configured to be slidably disposed within the continuous lumen of the inner shaft component and removable therefrom, the needle component having a curved distal end,
   wherein in a first configuration of the apparatus the curved distal end of the needle component is held in a straightened form within the needle housing of the inner shaft component and wherein in a second configuration of the apparatus the curved distal end of the needle component extends from the side port of the outer shaft component and bends from the longitudinal axis of the apparatus, and
   wherein the body portion of the inner shaft component includes a polymeric tube and the needle housing is formed from a tube of a shape memory material, a proximal end of the needle housing including two opposing tabs attached to the distal end of the body portion of the inner shaft component.

13. The apparatus of claim 12, wherein the curved distal end of the needle component has the same curvature as the curved distal portion of the inner shaft component and a distal tip of the needle component is configured to penetrate a wall of the vessel.

14. The apparatus of claim 12, wherein the outer shaft component includes at least one balloon disposed proximal to the distal end thereof and an inflation lumen in fluid communication with the at least one balloon.

15. An apparatus for bypassing an occlusion in a blood vessel comprising:
   an outer shaft component having a side port proximal to a distal end thereof and at least one balloon disposed proximal to the distal end thereof, wherein the outer shaft component defines an inflation lumen in fluid communication with the at least one balloon and a guidewire lumen extending at least along a distal portion thereof;
   an inner shaft component disposed within the outer shaft component and defining a continuous lumen therethrough, the inner shaft component having a body portion that extends substantially parallel with a longitudinal axis of the apparatus and a needle housing distally extending from a distal end of the body portion, the needle housing including a curved distal portion that bends from the longitudinal axis of the apparatus and terminates at the side port of the outer shaft component and a transition portion positioned between the body portion of the inner shaft component and the curved distal portion of the needle housing, wherein the transition portion has a variable flexibility along a length thereof length that decreases in a distal direction; and a needle component configured to be slidably disposed within the continuous lumen of the inner shaft component and removable therefrom, the needle component having a curved distal end with the same curvature as the curved distal portion of the inner shaft component, wherein the transition portion includes a plurality of apertures configured to provide the transition portion with the variable flexibility and wherein the plurality of apertures each have an hourglass shape with a waist region positioned between a top region and a bottom region, each hourglass-shaped aperture extending around an outer surface of the needle housing with a bridge area being defined between the top region and the bottom region thereof, and wherein adjacent hourglass-shaped apertures are positioned such that a bridge area of a first hourglass-shaped aperture longitudinally aligns with a waist region of a second hourglass-shaped aperture.

16. The apparatus of claim 15, wherein the at least one balloon includes a first lateral balloon and a second lateral balloon disposed in parallel on opposing sides of the outer shaft component.

17. The apparatus of claim 15, wherein the body portion of the inner shaft component is a polymeric tube and the needle housing is formed from a tube of a shape memory material, the transition portion of the needle housing including a plurality of apertures configured to provide the transition portion with the variable flexibility.

* * * * *